(12) United States Patent
Ashleigh et al.

(10) Patent No.: US 11,903,844 B2
(45) Date of Patent: *Feb. 20, 2024

(54) DEVICE AND METHOD FOR DEPLOYMENT OF AN ANCHORING DEVICE FOR INTERVERTEBRAL SPINAL FUSION

(71) Applicant: GLOBUS MEDICAL, INC., Audubon, PA (US)

(72) Inventors: Michael Ashleigh, Phoenixville, PA (US); Noah Hansell, King of Prussia, PA (US); Anand Balasubramanian, Collegeville, PA (US); Kurt Faulhaber, Renton, WA (US)

(73) Assignee: Globus Medical, Inc., Audubon, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/822,858

(22) Filed: Aug. 29, 2022

(65) Prior Publication Data

US 2022/0409393 A1 Dec. 29, 2022

Related U.S. Application Data

(63) Continuation of application No. 16/553,301, filed on Aug. 28, 2019, now Pat. No. 11,452,610, which is a
(Continued)

(51) Int. Cl.
*A61F 2/44* (2006.01)
*A61F 2/46* (2006.01)
*A61F 2/30* (2006.01)

(52) U.S. Cl.
CPC ............ *A61F 2/4455* (2013.01); *A61F 2/447* (2013.01); *A61F 2/4611* (2013.01); *A61F 2/4603* (2013.01); *A61F 2002/304* (2013.01); *A61F 2002/30197* (2013.01); *A61F 2002/30383* (2013.01); *A61F 2002/30405* (2013.01); *A61F 2002/30525* (2013.01); *A61F 2002/30556* (2013.01); *A61F 2002/30571* (2013.01); *A61F 2002/30579* (2013.01); *A61F 2002/30593* (2013.01);
(Continued)

(58) Field of Classification Search
CPC ....... A61F 2/4455; A61F 2/447; A61F 2/4611
See application file for complete search history.

(56) References Cited

U.S. PATENT DOCUMENTS

| 4,349,921 A | 9/1982 | Kuntz |
| 4,599,086 A | 7/1986 | Doty |

(Continued)

FOREIGN PATENT DOCUMENTS

| CA | 2088066 A1 | 1/1992 |
| CH | 708531 A2 | 3/2015 |

(Continued)

*Primary Examiner* — Si Ming Ku

(57) ABSTRACT

Devices and methods for intervertebral spinal fusion of adjacent intervertebral bodies are provided. An intervertebral spacer is positioned within a narrow disc space between adjacent intervertebral bodies of a patient. The spacer is arranged with upper and lower guides. The guides are adapted to simultaneously guide the deployment of upper and lower anchors of an anchoring device into their respective intervertebral bodies. The spacer is also adapted to lock the upper and lower anchors to the spacer in the deployed position.

15 Claims, 35 Drawing Sheets

Related U.S. Application Data continuation of application No. 15/148,018, filed on May 6, 2016, now Pat. No. 10,433,975, which is a continuation-in-part of application No. 14/718,514, filed on May 21, 2015, now Pat. No. 10,376,378.

(52) U.S. Cl.
CPC ............... *A61F 2002/30828* (2013.01); *A61F 2002/30836* (2013.01); *A61F 2002/30845* (2013.01); *A61F 2002/30904* (2013.01); *A61F 2002/4627* (2013.01); *A61F 2220/0008* (2013.01)

(56) References Cited

U.S. PATENT DOCUMENTS

| | | | |
|---|---|---|---|
| 4,863,476 | A | 9/1989 | Shepperd |
| 4,863,477 | A | 9/1989 | Monson |
| 5,123,926 | A | 6/1992 | Pisharodi |
| 5,290,312 | A | 3/1994 | Kojimoto et al. |
| 5,306,310 | A | 4/1994 | Siebels |
| 5,375,823 | A | 12/1994 | Navas |
| 5,390,683 | A | 2/1995 | Pisharodi |
| 5,522,899 | A | 6/1996 | Michelson |
| 5,534,030 | A | 7/1996 | Navarro et al. |
| 5,554,191 | A | 9/1996 | Lahille et al. |
| 5,571,192 | A | 11/1996 | Schonhoffer |
| 5,645,596 | A | 7/1997 | Kim |
| 5,653,763 | A | 8/1997 | Errico et al. |
| 5,665,122 | A | 9/1997 | Kambin |
| 5,676,701 | A | 10/1997 | Yuan et al. |
| 5,849,004 | A | 12/1998 | Bramlet |
| 6,039,761 | A | 3/2000 | Li et al. |
| 6,045,579 | A | 4/2000 | Hochschuler et al. |
| 6,080,193 | A | 6/2000 | Hochschuler et al. |
| 6,099,531 | A | 8/2000 | Bonutti |
| 6,126,689 | A | 10/2000 | Brett |
| 6,176,882 | B1 | 1/2001 | Biedermann et al. |
| 6,258,125 | B1 | 7/2001 | Paul et al. |
| 6,447,546 | B1 | 9/2002 | Bramlet et al. |
| 6,558,423 | B1 | 5/2003 | Michelson |
| 6,562,074 | B2 | 5/2003 | Gerbec et al. |
| 6,576,016 | B1 | 6/2003 | Hochschuler et al. |
| 6,554,863 | B2 | 8/2003 | Paul et al. |
| 6,641,614 | B1 | 11/2003 | Wagner et al. |
| 6,648,917 | B2 | 11/2003 | Gerbec et al. |
| 6,666,891 | B2 | 12/2003 | Boehm, Jr. et al. |
| 6,692,495 | B1 | 2/2004 | Zacouto |
| 6,706,070 | B1 | 3/2004 | Wagner et al. |
| 6,752,832 | B2 | 6/2004 | Ulrich |
| 6,814,756 | B1 | 11/2004 | Michelson |
| 6,830,589 | B2 | 12/2004 | Erickson |
| 6,849,093 | B2 | 2/2005 | Michelson |
| 6,852,129 | B2 | 2/2005 | Gerbec et al. |
| 6,863,673 | B2 | 3/2005 | Gerbec et al. |
| 6,881,228 | B2 | 4/2005 | Zdeblick et al. |
| 7,018,415 | B1 | 3/2006 | McKay |
| 7,070,598 | B2 | 7/2006 | Lim et al. |
| 7,204,853 | B2 | 4/2007 | Gordon |
| 7,217,291 | B2 | 5/2007 | Zucherman et al. |
| 7,282,063 | B2 | 10/2007 | Cohen et al. |
| 7,316,714 | B2 | 1/2008 | Gordon |
| 7,473,276 | B2 | 1/2009 | Aebi et al. |
| 7,547,325 | B2 | 6/2009 | Biedermann et al. |
| 7,621,953 | B2 | 11/2009 | Braddock, Jr. et al. |
| 7,641,693 | B2 | 1/2010 | Gutlin et al. |
| 7,682,396 | B2 | 3/2010 | Beaurain et al. |
| 7,695,516 | B2 | 4/2010 | Zeegers |
| 7,749,270 | B2 | 7/2010 | Peterman |
| 7,753,958 | B2 | 7/2010 | Gordon |
| 7,771,473 | B2 | 8/2010 | Thramann |
| 7,780,732 | B2 | 8/2010 | Abernathie |
| 7,799,081 | B2 | 9/2010 | McKinley |
| 7,815,683 | B2 | 10/2010 | Melkent et al. |
| 7,837,734 | B2 | 11/2010 | Zucherman et al. |
| 7,875,078 | B2 | 1/2011 | Wysocki et al. |
| 7,901,409 | B2 | 3/2011 | Canaveral et al. |
| 7,909,869 | B2 | 3/2011 | Gordon |
| 7,951,199 | B2 | 5/2011 | Miller |
| 7,985,256 | B2 | 7/2011 | Grotz et al. |
| 8,062,375 | B2 | 11/2011 | Glerum |
| 8,070,813 | B2 | 12/2011 | Grotz et al. |
| 8,123,810 | B2 | 2/2012 | Gordon |
| 8,137,405 | B2 | 3/2012 | Kostuik et al. |
| 8,192,495 | B2 | 6/2012 | Simpson et al. |
| 8,303,663 | B2 | 11/2012 | Jimenez et al. |
| 8,343,219 | B2 | 1/2013 | Allain et al. |
| 8,377,140 | B2 | 2/2013 | DeFalco et al. |
| 8,394,129 | B2 | 3/2013 | Lopez et al. |
| 8,394,143 | B2 | 3/2013 | Grotz et al. |
| 8,435,296 | B2 | 5/2013 | Kadaba et al. |
| 8,454,695 | B2 | 6/2013 | Grotz et al. |
| 8,460,388 | B2 | 6/2013 | Kirwan et al. |
| 8,617,245 | B2 | 12/2013 | Brett |
| 8,641,766 | B2 | 2/2014 | Donner et al. |
| 8,647,386 | B2 | 2/2014 | Gordon |
| 8,685,104 | B2 | 4/2014 | Lee et al. |
| 8,696,751 | B2 | 4/2014 | Ashley et al. |
| 8,771,360 | B2 | 7/2014 | Jimenez et al. |
| 8,894,710 | B2 | 11/2014 | Simpson et al. |
| 8,932,355 | B2 | 1/2015 | Grotz et al. |
| 8,940,049 | B1 | 1/2015 | JImenez et al. |
| 8,956,413 | B2 | 2/2015 | Ashley et al. |
| 8,968,405 | B2 | 3/2015 | Kirwan et al. |
| 8,992,620 | B2 | 3/2015 | Ashley et al. |
| 9,028,550 | B2 | 5/2015 | Shulock et al. |
| 9,039,774 | B2 | 5/2015 | Chataigner et al. |
| 9,044,337 | B2 | 6/2015 | Dinville et al. |
| 9,161,842 | B2 | 10/2015 | Chin et al. |
| 9,173,745 | B2 | 11/2015 | Dinville et al. |
| 9,358,125 | B2 | 6/2016 | JImenez et al. |
| 9,532,883 | B2 | 1/2017 | McLuen et al. |
| 9,622,878 | B2 | 4/2017 | Grotz |
| 2002/0045945 | A1 | 4/2002 | Liu |
| 2002/0068976 | A1 | 6/2002 | Jackson |
| 2002/0068977 | A1 | 6/2002 | Jackson |
| 2003/0176926 | A1 | 9/2003 | Boehm et al. |
| 2003/0187436 | A1 | 10/2003 | Bolger et al. |
| 2004/0030387 | A1 | 2/2004 | Landry et al. |
| 2004/0049271 | A1 | 3/2004 | Biedermann |
| 2004/0054412 | A1 | 3/2004 | Gerbec et al. |
| 2004/0087947 | A1 | 5/2004 | Lim et al. |
| 2004/0153065 | A1 | 8/2004 | Lim |
| 2005/0021041 | A1 | 1/2005 | Michelson |
| 2005/0021145 | A1 | 1/2005 | de Villiers et al. |
| 2005/0033432 | A1 | 2/2005 | Gordon |
| 2005/0049590 | A1 | 3/2005 | Alleyne et al. |
| 2005/0080422 | A1 | 4/2005 | Otte et al. |
| 2005/0113916 | A1 | 5/2005 | Branch |
| 2005/0149188 | A1 | 7/2005 | Cook |
| 2005/0171541 | A1 | 8/2005 | Boehm |
| 2005/0251258 | A1 | 11/2005 | Jackson |
| 2005/0273171 | A1 | 12/2005 | Gordon |
| 2005/0273174 | A1 | 12/2005 | Gordon |
| 2005/0278026 | A1 | 12/2005 | Gordon |
| 2005/0283244 | A1 | 12/2005 | Gordon |
| 2005/0283245 | A1 | 12/2005 | Gordon |
| 2006/0004453 | A1 | 1/2006 | Bartish, Jr. et al. |
| 2006/0015184 | A1 | 1/2006 | Winterbottom et al. |
| 2006/0058878 | A1 | 3/2006 | Michelson |
| 2006/0084986 | A1 | 4/2006 | Grinberg et al. |
| 2006/0122701 | A1 | 6/2006 | Kister |
| 2006/0129244 | A1 | 6/2006 | Ensign |
| 2006/0142859 | A1 | 6/2006 | Mcluen |
| 2006/0149385 | A1 | 7/2006 | Mckay |
| 2006/0195192 | A1 | 8/2006 | Gordon et al. |
| 2006/0229729 | A1 | 10/2006 | Gordon |
| 2006/0241770 | A1 | 10/2006 | Rhoda et al. |
| 2006/0253201 | A1 | 11/2006 | Mcluen |
| 2007/0043442 | A1 | 2/2007 | Abernathie |
| 2007/0050030 | A1 | 3/2007 | Kim |
| 2007/0050032 | A1 | 3/2007 | Gittings et al. |
| 2007/0055377 | A1 | 3/2007 | Hanson et al. |
| 2007/0191951 | A1 | 8/2007 | Branch |

(56) References Cited

U.S. PATENT DOCUMENTS

| | | |
|---|---|---|
| 2007/0255415 A1 | 11/2007 | Edie et al. |
| 2007/0270960 A1 | 11/2007 | Bonin, Jr. et al. |
| 2007/0270963 A1 | 11/2007 | Melkent et al. |
| 2007/0270968 A1 | 11/2007 | Baynham |
| 2008/0021559 A1 | 1/2008 | Thramann |
| 2008/0065222 A1 | 3/2008 | Hamada |
| 2008/0114467 A1 | 5/2008 | Capote et al. |
| 2008/0140207 A1 | 6/2008 | Olmos et al. |
| 2008/0147194 A1 | 6/2008 | Grotz et al. |
| 2008/0161933 A1 | 7/2008 | Grotz et al. |
| 2008/0167657 A1 | 7/2008 | Greenhalgh |
| 2008/0183204 A1 | 7/2008 | Greenhalgh et al. |
| 2008/0221694 A1 | 9/2008 | Warnick et al. |
| 2008/0275455 A1 | 11/2008 | Berry et al. |
| 2008/0281346 A1 | 11/2008 | Greenhalgh et al. |
| 2008/0288073 A1 | 11/2008 | Renganath et al. |
| 2008/0300598 A1 | 12/2008 | Barreiro et al. |
| 2008/0306488 A1 | 12/2008 | Altarac et al. |
| 2008/0319487 A1 | 12/2008 | Fielding et al. |
| 2008/0319549 A1 | 12/2008 | Greenhalgh et al. |
| 2009/0024217 A1 | 1/2009 | Levy et al. |
| 2009/0062833 A1 | 3/2009 | Song |
| 2009/0076616 A1 | 3/2009 | Duggal et al. |
| 2009/0125062 A1 | 5/2009 | Amin |
| 2009/0149956 A1 | 6/2009 | Greenhalgh et al. |
| 2009/0149959 A1 | 6/2009 | Conner et al. |
| 2009/0204218 A1 | 8/2009 | Richelsoph |
| 2009/0222100 A1 | 9/2009 | Cipoletti et al. |
| 2009/0240334 A1 | 9/2009 | Richelsoph |
| 2009/0265007 A1 | 10/2009 | Colleran |
| 2009/0270989 A1 | 10/2009 | Conner et al. |
| 2009/0281628 A1 | 11/2009 | Oglaza et al. |
| 2009/0292361 A1 | 11/2009 | Lopez |
| 2009/0299478 A1 | 12/2009 | Carls et al. |
| 2009/0312763 A1 | 12/2009 | McCormack |
| 2010/0049324 A1 | 2/2010 | Valdevit |
| 2010/0070041 A1 | 3/2010 | Peterman |
| 2010/0082109 A1 | 4/2010 | Greenhalgh et al. |
| 2010/0145455 A1 | 6/2010 | Simpson et al. |
| 2010/0160984 A1 | 6/2010 | Berry et al. |
| 2010/0179657 A1 | 7/2010 | Greenhalgh et al. |
| 2010/0211176 A1 | 8/2010 | Greenhalgh |
| 2010/0222816 A1 | 9/2010 | Gabelberger et al. |
| 2010/0286783 A1 | 11/2010 | Lechmann et al. |
| 2011/0035011 A1 | 2/2011 | Cain |
| 2011/0093074 A1 | 4/2011 | Glerum et al. |
| 2011/0160861 A1 | 6/2011 | Jimenez et al. |
| 2011/0172774 A1 | 7/2011 | Varela |
| 2011/0178599 A1 | 7/2011 | Brett |
| 2011/0276142 A1 | 11/2011 | Niemiec et al. |
| 2011/0301713 A1 | 12/2011 | Theofilos |
| 2011/0319997 A1 | 12/2011 | Glerum et al. |
| 2012/0035729 A1 | 2/2012 | Glerum et al. |
| 2012/0059470 A1 | 3/2012 | Weiman |
| 2012/0059472 A1 | 3/2012 | Weiman |
| 2012/0078371 A1 | 3/2012 | Gamache et al. |
| 2012/0109308 A1 | 5/2012 | Lechmann et al. |
| 2012/0130496 A1 | 5/2012 | Duffield et al. |
| 2012/0150229 A1 | 6/2012 | Hess |
| 2012/0165945 A1 | 6/2012 | Hansell et al. |
| 2012/0185049 A1 | 7/2012 | Varela |
| 2012/0209386 A1 | 8/2012 | Triplett et al. |
| 2012/0215313 A1 | 8/2012 | Saidha et al. |
| 2012/0226357 A1 | 9/2012 | Varela |
| 2012/0265309 A1 | 10/2012 | Glerum et al. |
| 2012/0277861 A1 | 11/2012 | Steele et al. |
| 2012/0277870 A1 | 11/2012 | Wolters et al. |
| 2012/0323329 A1 | 12/2012 | Jimenez et al. |
| 2012/0330426 A1 | 12/2012 | McLaughlin et al. |
| 2013/0023993 A1 | 1/2013 | Weiman |
| 2013/0023994 A1 | 1/2013 | Glerum |
| 2013/0150968 A1 | 6/2013 | Dinville et al. |
| 2013/0158663 A1 | 6/2013 | Miller et al. |
| 2013/0158669 A1 | 6/2013 | Sungarian et al. |
| 2013/0197647 A1 | 8/2013 | Wolters et al. |
| 2013/0211526 A1 | 8/2013 | Alheidt et al. |
| 2013/0226300 A1 | 8/2013 | Chataigner et al. |
| 2013/0245767 A1 | 9/2013 | Lee et al. |
| 2013/0274883 A1 | 10/2013 | McLuen et al. |
| 2014/0067071 A1 | 3/2014 | Weiman et al. |
| 2014/0088711 A1* | 3/2014 | Chin .................. A61F 2/30749 623/17.16 |
| 2014/0088714 A1 | 3/2014 | Miller et al. |
| 2014/0100662 A1 | 4/2014 | Patterson et al. |
| 2014/0163683 A1 | 6/2014 | Seifert et al. |
| 2014/0180417 A1 | 6/2014 | Bergey |
| 2015/0051702 A1 | 2/2015 | Chataigner et al. |
| 2015/0057754 A1 | 2/2015 | Reed et al. |
| 2015/0066145 A1 | 3/2015 | Rogers et al. |
| 2015/0088258 A1 | 3/2015 | Jimenez et al. |
| 2015/0127107 A1 | 5/2015 | Kim et al. |
| 2015/0134064 A1 | 5/2015 | Grotz et al. |
| 2015/0209089 A1 | 7/2015 | Chataigner et al. |
| 2015/0216676 A1 | 8/2015 | Shulock et al. |
| 2015/0289988 A1 | 10/2015 | Ashley et al. |
| 2015/0305887 A1 | 10/2015 | McAtamney et al. |
| 2015/0320568 A1 | 11/2015 | Ameil et al. |
| 2015/0374508 A1 | 12/2015 | Sandul |
| 2016/0166396 A1 | 6/2016 | McClintock |
| 2016/0324654 A1 | 11/2016 | Loebl et al. |
| 2016/0338845 A1 | 11/2016 | Ashleigh |
| 2017/0100258 A1 | 4/2017 | Jimenez et al. |
| 2017/0119543 A1 | 5/2017 | Dietzel et al. |

FOREIGN PATENT DOCUMENTS

| | | |
|---|---|---|
| DE | 4012622 C1 | 7/1991 |
| DE | 4327054 C1 | 4/1995 |
| EP | 0576379 B1 | 6/1993 |
| EP | 0610837 B1 | 7/1994 |
| EP | 1378202 A1 | 1/2004 |
| EP | 3111896 A1 | 1/2017 |
| FR | 2794968 A1 | 12/2000 |
| JP | 2000-513263 A | 10/2000 |
| JP | 2005523732 A | 8/2005 |
| JP | 2013516206 A | 5/2013 |
| JP | 2015501189 A | 1/2015 |
| JP | 2015054235 A | 3/2015 |
| JP | 2015507989 A | 3/2015 |
| JP | 2015510817 A | 4/2015 |
| JP | 2015529149 A | 10/2015 |
| JP | 2015536807 A | 12/2015 |
| KR | 200290058 Y1 | 9/2002 |
| SU | 1424826 A1 | 9/1988 |
| WO | 9201428 A1 | 2/1992 |
| WO | 9525485 A1 | 9/1995 |
| WO | 9942062 A1 | 8/1999 |
| WO | 1999042062 A1 | 8/1999 |
| WO | 1999066867 A1 | 12/1999 |
| WO | 2002045625 A1 | 6/2002 |
| WO | 2004019829 A1 | 3/2004 |
| WO | 2004069033 A2 | 8/2004 |
| WO | 2006045094 A2 | 4/2006 |
| WO | 2006047587 A2 | 5/2006 |
| WO | 2006113080 A2 | 10/2006 |
| WO | 2008044057 A1 | 4/2008 |
| WO | 2008134515 A1 | 11/2008 |
| WO | 2009114381 A1 | 9/2009 |
| WO | 2010103344 A1 | 9/2010 |
| WO | 2012031267 A1 | 3/2012 |
| WO | 2012117312 A2 | 9/2012 |
| WO | 2014047612 A1 | 3/2014 |
| WO | 2015009793 A1 | 1/2015 |
| WO | 2015164707 A1 | 10/2015 |
| WO | 2016187604 A1 | 11/2016 |

* cited by examiner

DEVICE AND METHOD FOR DEPLOYMENT OF AN ANCHORING DEVICE FOR INTERVERTEBRAL SPINAL FUSION

CROSS-REFERENCE TO RELATED APPLICATION

The present application is a Continuation of U.S. patent application Ser. No. 16/553,301 filed Aug. 28, 2019 (published as U.S. Pat. Pub. No. 2020-0008955), which is a Continuation of U.S. patent application Ser. No. 15/148,018 filed on May 6, 2016 (now U.S. Pat. No. 10,433,975), which is a Continuation-in-Part of U.S. patent application Ser. No. 14/718,514 filed May 21, 2015 (now U.S. Pat. No. 10,376,378), all of which are incorporated herein by reference in their entirety for all purposes.

FIELD OF THE INVENTION

The present invention relates generally to intervertebral spacers for fusing adjacent vertebrae, and more particularly to a device and methods for doing so.

BACKGROUND

Intervertebral spinal fusion is well known in the art. In the prior art, an intervertebral spacer is implanted between two adjacent intervertebral bodies. The spacer allows a surgeon to deposit bone graft between the problem vertebrae in order to fuse the vertebrae together. To achieve proper fusion, the implanted spacer must be securely anchored between the vertebrae such that there is little to no movement once implanted. Protrusions arranged on the superior and inferior surfaces of the spacer provide a means to stabilize the spacer between the vertebrae. However, it has been discovered that spacers stabilized in this way may still move due to the stress exerted on the implanted spacer when the patient moves. Other commonly employed stabilizing techniques include pedicle screws and rods. In this technique, pedicle screws are independently screwed into two or three spine segments. A short rod is then used to connect the pedicle screws to prevent motion at the segments that are being fused. However, this technique is time consuming because the pedicle screws need to be independently screwed into the vertebrae. It also requires the surgeon to make large/numerous incisions in the patient to insert the pedicle screws. Because of these deficiencies in the prior art, there exists a need to provide a more effective and efficient way of stabilizing adjacent vertebrae in the field of intervertebral spinal fusion.

SUMMARY

To meet this and other needs, devices and methods for intervertebral spinal fusion of adjacent intervertebral bodies are provided. In one aspect, the present invention provides a way to stabilize adjacent vertebrae without some of the deficiencies discussed above.

In one illustrative embodiment, a spacer is provided with an upper guide and a lower guide. The upper and lower guides are adapted to guide the simultaneous deployment of a respective upper anchor and lower anchor of an anchoring device when force is applied thereto. More precisely, force is simultaneously applied to a proximal portion of the upper and lower anchors. The force simultaneously deploys the upper and lower anchors into their respective intervertebral bodies. The upper and lower anchors are constructed and dimensioned in such a way to pierce and penetrate into their respective vertebrae. The combination of the anchors and the protrusions arranged on the surfaces of the spacer provides additional stabilization of the implanted spacer.

In another illustrative embodiment, an intervertebral fusion device includes a spacer having superior and inferior surfaces adapted to be implanted between an upper vertebral body and a lower vertebral body and lateral sides surfaces connecting the superior and inferior surfaces; and an anchoring device having a body with an anchor tip and a proximal end, located proximal from anchor tip, and a central groove to define the body as a generally V-shaped body, wherein the proximal end includes two enlarged proximal tips separated by the central groove, the anchoring device being movable between a first position wherein the anchor tip is disposed inside the spacer and a second position wherein the anchor tip is extended outwardly from the spacer, wherein the anchoring device is centrally positioned between the lateral side surfaces of the spacer.

In yet another illustrative embodiment, an intervertebral fusion device includes a body having a superior surface and an opposing inferior surface and a proximal end and a distal end, each extending between the superior surface and the inferior surface, wherein the body further includes an upper track extending from the proximal end to the superior surface and a lower track extending from the proximal end to the inferior surface; an upper anchor having an upper anchor tip sliding disposed along the upper track such that upper anchor tip is movable from a first position inside the body to a second position, extending outwardly from the superior surface; and a lower anchor having a lower anchor tip sliding disposed along the lower track such that lower anchor tip is movable from a first position inside the body to a second position, extending outwardly from the inferior surface.

In yet another illustrative embodiment, an intervertebral fusion includes a body having a superior surface, an opposing inferior surface, and a proximal end extending between the superior surface and the inferior surface, an upper passage extending between the superior surface and the proximal end; and a lower passage extending between the inferior surface and the proximal end; an upper anchor sliding disposed in the upper passage between a first upper anchor position and a second upper anchor position, the upper anchor having an upper anchor tip disposed within the body when the upper anchor is in the first upper anchor position and wherein the upper anchor tip extends outwardly from the superior surface when the upper anchor is in the second upper anchor position; and a lower anchor sliding disposed in the lower passage between a first lower anchor position and a second lower anchor position, the lower anchor having a lower anchor tip disposed within the body when the lower anchor is in the first lower anchor position and wherein the lower anchor tip extends outwardly from the inferior surface when the lower anchor is in the second lower anchor position.

For the purpose of the following description and the appended claims, "proximal" and its inflected forms are defined as the part, portion, section, etc., of an object that is closest to the person using that object.

For the purpose of the following description and the appended claims, "distal" and its inflected forms are defined as the part, portion, section, etc., of an object that is furthest away to the person using that object.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings.

DETAILED DESCRIPTION

Figure 1A:
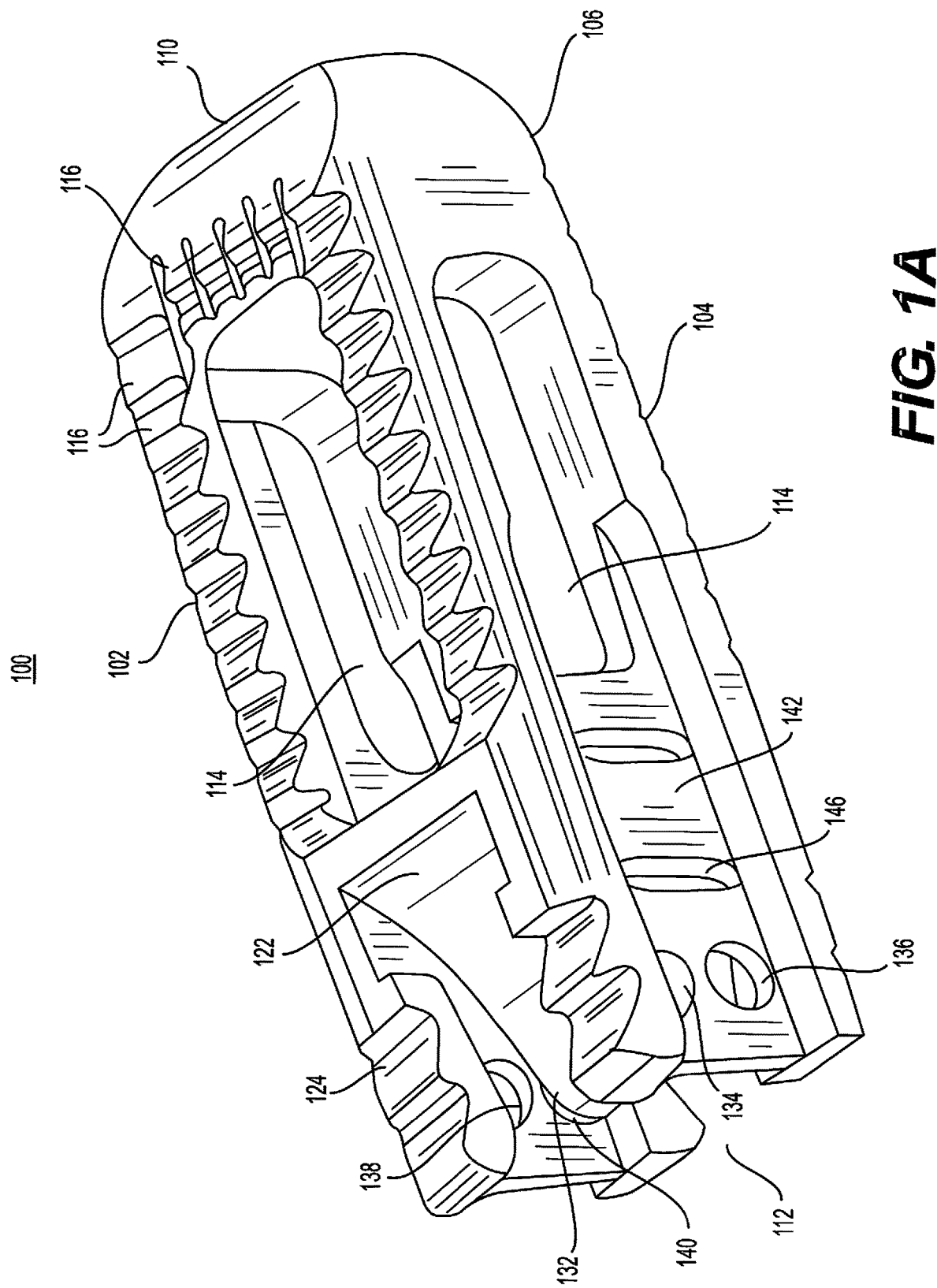
FIG. 1A depicts a perspective view of an intervertebral spacer in accordance with an illustrative embodiment of the present invention.

In the drawings, like numerals indicate like elements throughout. Certain terminology is used herein for convenience only and is not to be taken as a limitation on the present invention. The terminology includes the words specifically mentioned, derivatives thereof and words of similar import. The embodiments illustrated below are not intended to be exhaustive or to limit the invention to the precise form disclosed. These embodiments are chosen and described to best explain the principle of the invention and its application and practical use and to enable others skilled in the art to best utilize the invention.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

As used in this application, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

Additionally, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Unless explicitly stated otherwise, each numerical value and range should be interpreted as being approximate as if the word "about" or "approximately" preceded the value of the value or range.

The use of figure numbers and/or figure reference labels in the claims is intended to identify one or more possible embodiments of the claimed subject matter in order to facilitate the interpretation of the claims. Such use is not to be construed as necessarily limiting the scope of those claims to the embodiments shown in the corresponding figures.

It should be understood that the steps of the exemplary methods set forth herein are not necessarily required to be performed in the order described, and the order of the steps of such methods should be understood to be merely exemplary. Likewise, additional steps may be included in such methods, and certain steps may be omitted or combined, in methods consistent with various embodiments of the present invention.

Although the elements in the following method claims, if any, are recited in a particular sequence with corresponding labeling, unless the claim recitations otherwise imply a particular sequence for implementing some or all of those elements, those elements are not necessarily intended to be limited to being implemented in that particular sequence.

Figure 1B:
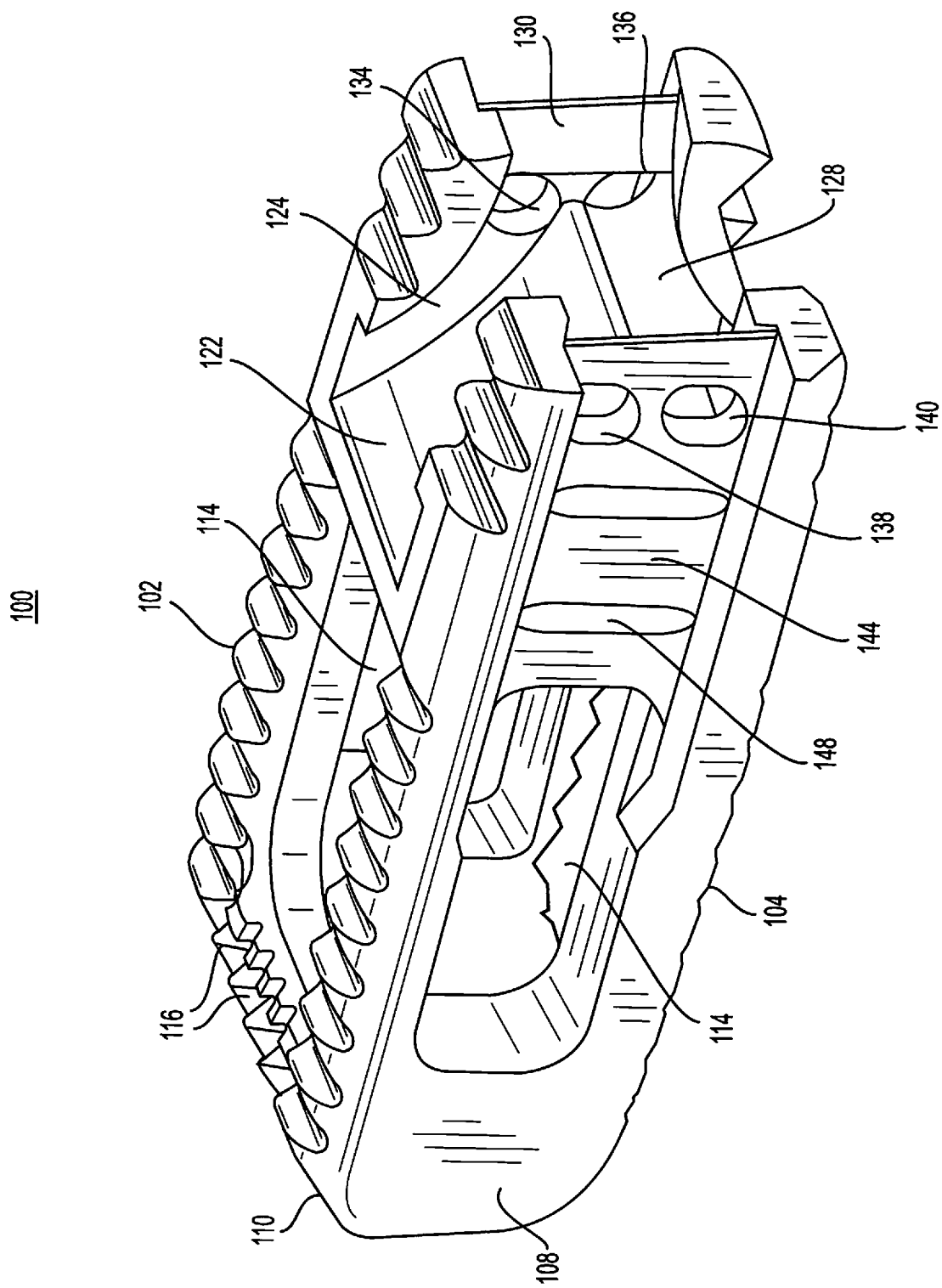
FIG. 1B depicts another perspective view of the intervertebral spacer of FIG. 1A.

FIGS. 1A and 1B depict perspective views of intervertebral spacer 100 in accordance with an illustrative embodiment of the present invention. Spacer 100 generally has a rectangular shape, but the present invention is not limited to such a shape. Spacer 100 can have any shape, size, or combination thereof to meet the needs of a spinal fusion candidate.

As depicted in FIGS. 1A and 1B, spacer 100 comprises superior surface 102, inferior surface 104, lateral surfaces 106 and 108, distal portion 110, and proximal portion 112. Inferior surface 104 is a mirror image of superior surface 102 and lateral surface 108 is a mirror image of lateral surface 106. Spacer 100 is preferably formed from titanium alloy but other biocompatible materials (e.g., polyetheretherketone (PEEK), other surgical grade metals, alloys, or a combination thereof) can also be used to form spacer 100.

Beginning at distal portion 110, spacer 100 is constructed to have a tapered end that narrows towards the distal most end. This design helps facilitate easier entry of spacer 100 into the narrow disc space arranged between two adjacent vertebral bodies.

Figure 2A:
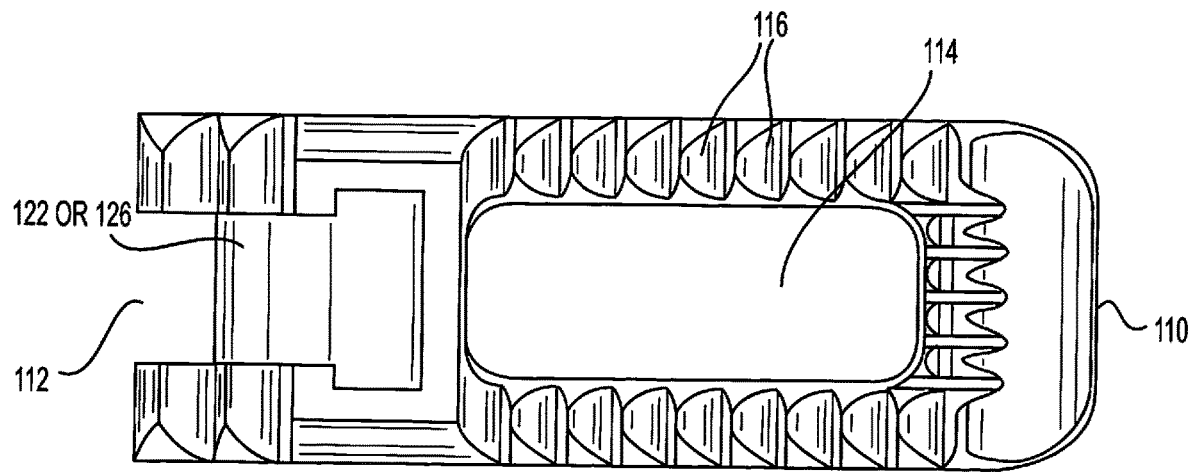
FIG. 2A depicts a top view of the intervertebral spacer of FIGS. 1A and 1B.
Figure 2B:
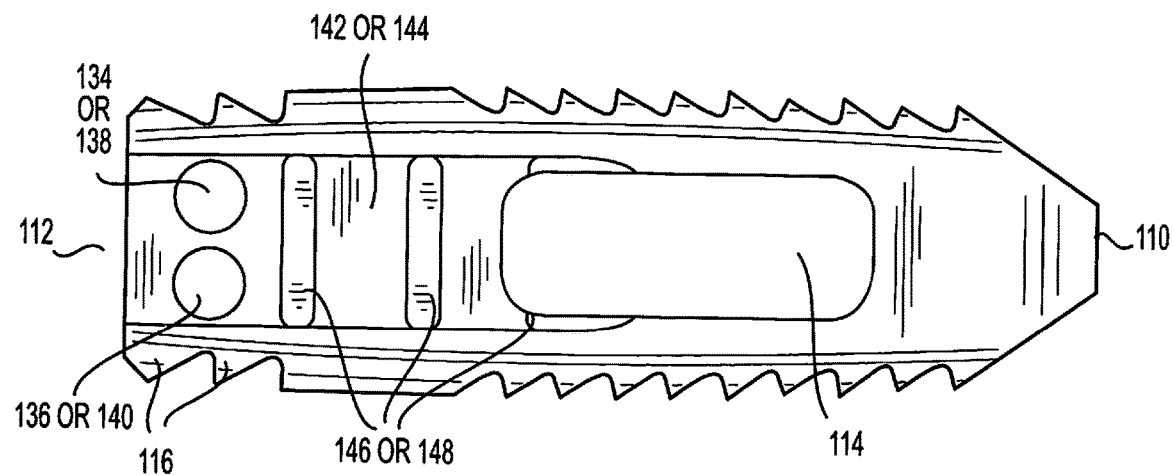
FIG. 2B depicts a side view of the intervertebral spacer of FIGS. 1A and 1B.

To fuse the adjacent vertebrae together, bone graft is used. For this purpose, the body of spacer 100 is provided with through-hole 114. The through-hole extends through the center of surfaces 102, 104, 106, and 108 and is adapted to receive the bone graft for fusing the adjacent vertebrae. In the illustrative embodiment, through-hole 114 generally has a rectangular shape. However, those skilled in the art will appreciate after reading this disclosure that through-hole 114 can have any shape, size, or a combination thereof. As further depicted in FIGS. 1A and 1B, surfaces 102 and 104 are provided with a plurality of protrusions or teeth 116 to help prevent spacer 100 from expulsion after being implanted between the adjacent vertebrae. It will be appreciated by those skilled in the art, after reading this disclosure, that teeth 116 can be angled in any number of degrees (e.g., 45°, 90°, etc.) and can have any number of orientations without departing from the scope of the present invention. Through-hole 114 and teeth 116 can be seen more clearly in FIGS. 2A and 2B.

Turning now to proximal portion 112, upper and lower guides are provided to respectively guide the deployment of upper anchor 118 and lower anchor 120 into their respective vertebral bodies. The upper and lower anchors will be discussed in more detail below, with respect to FIGS. 3A and 3B. In the illustrative embodiment, the upper guide is characterized by an upper inclined surface 122 (e.g., a curvilinear surface, etc.) and an upper pair of oppositely positioned lateral recesses 124. Because the lower guide is a mirror image of the upper guide, the lower guide is also characterized by a lower inclined surface 126 and a lower pair of oppositely positioned lateral recesses 128. The upper and lower pair of lateral recesses 124 and 128 are dimensioned to respectively complement the arc, curvature, etc., of the upper and lower anchors. An advantage of recesses 124 and 128 is that they ensure that their respective anchors maintain a desired trajectory when impacted by an anchor driver. The recesses 124 and 128 also prevent their respective anchors from egressing out of spacer 100 when impacted by the anchor driver. These features and their advantages will be discussed in more detail below, with reference to FIGS. 4A and 4B.

Proximal portion 112 also comprises a pair of oppositely positioned lateral chamfers 130 and 132. Each of the lateral chamfers has a sloping edge and is positioned proximally to their respective locking recesses 134, 136, 138, and 140. As will be described in more detail below, with reference to FIGS. 6A-6D, the chamfer-recess combination is a mechanism that allows upper anchor 118 and lower anchor 120 to be locked to spacer 100 after deployment. It will be appreciated by those skilled in the art, after reading this disclosure, that locking recesses 134, 136, 138, 140 could be detents in some embodiments and through-holes in other embodiments.

Proximal portion 112 further comprises lateral surfaces 142 and 144 that are respectively constructed with gripper recesses 146 and 148. The gripper recesses are dimensioned and arranged to receive corresponding ribs of an implantation instrument employed by a surgeon. The ribs are adapted to fit squarely into their corresponding recesses so that spacer 100 can be securely gripped by the surgeon. It should be noted that gripping the spacer with an implantation instrument serves at least two purposes. First, it enables the surgeon to more easily orient spacer 100 in a desired position within the narrow disc space of the adjacent vertebrae. Secondly, it prevents spacer 100 from coming free from the implantation instrument while the surgeon is impacting the upper and lower anchors with an anchor driver. Although each of the lateral surfaces is depicted as having three gripping recesses, it will be appreciated by those skilled in the art that each of the lateral surfaces can have more or less gripper recesses than depicted. This feature of the present invention will be described in more detail below, with reference to FIGS. 5A-5D.

Figure 3A:
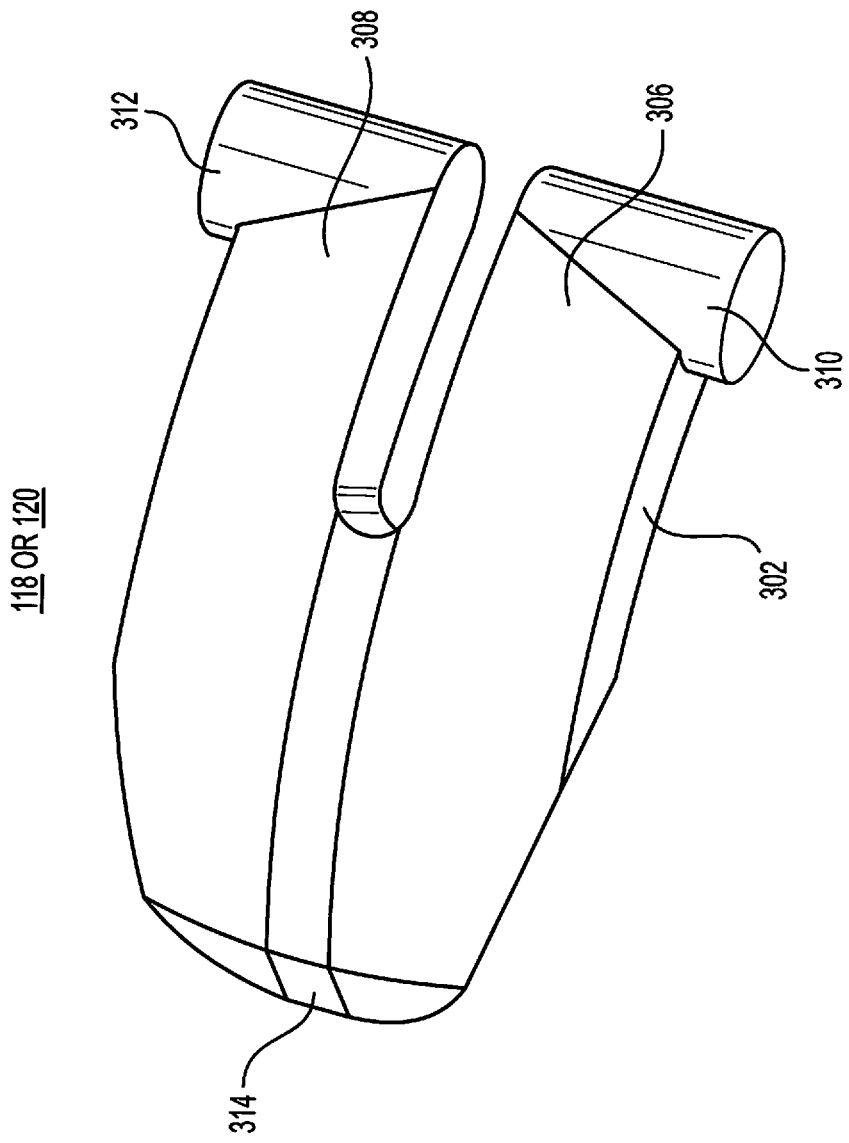
FIG. 3A depicts one side of an anchor in accordance with an illustrative embodiment of the present invention.
Figure 3B:
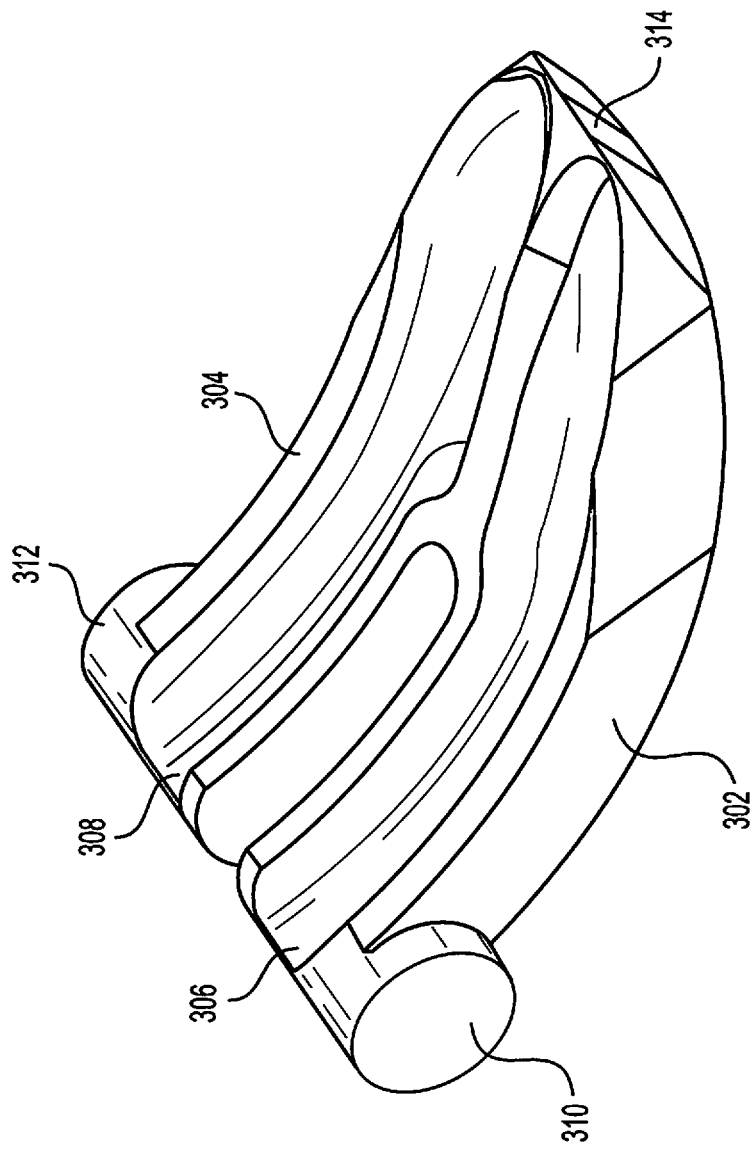
FIG. 3B depicts the other side of the anchor of FIG. 3A.

FIGS. 3A and 3B are perspective views of an anchor in accordance with an illustrative embodiment of the present invention. Since upper anchor 118 and lower anchor 120 have substantially the same physical and functional characteristics, thus being interchangeable, the following discussion of FIGS. 3A and 3B will use the word "anchor" to describe both the upper and lower anchors. Further, it should be noted that upper anchor 118 and lower anchor 120 (whether formed as independent pieces or as a single unitary piece) collectively define an anchoring device.

FIG. 3A depicts the surface of an anchor that is adapted to slide along an inclined surface of a guide (e.g., upper inclined surface 122 or lower inclined surface 126). In the illustrative embodiment, the anchor is constructed to have a curved or semi-curved surface that is contoured to be substantially the same as the inclined surface of the guide it slides on. The surface of the anchor is preferably smooth throughout its length in order to reduce the amount of friction drag produced when the surface slides along the inclined surface.

The anchor also comprises a pair of oppositely positioned lateral sides 302 and 304, which are adapted to slide into their respective lateral recesses (e.g., upper lateral recesses 124 or lower lateral recesses 128). The anchor is also constructed with a pair of flexible prongs 306 and 308, which respectively comprises lateral projections 310 and 312. The flexible prongs and lateral projections work in cooperation to lock the anchor to spacer 100 in a deployed position. The lateral sides, flexible prongs, and lateral projections of the anchor are also depicted in FIG. 3B.

To enable the anchor to penetrate a vertebral body, distal portion 314 of the anchor is tapered to form an edge. Since the anchor is made of titanium alloy, the distal portion of the anchor is sufficiently strong to pierce and penetrate through the endplate of the vertebral body. Although the anchor is preferably formed from titanium alloy, other biocompatible materials (e.g., polyetheretherketone (PEEK), other surgical grade metals, alloys, or a combination thereof) can be used to form the anchor.

It will be clear to those skilled in the art that the foregoing discussion of FIGS. 3A and 3B applies to both upper anchor 118 and lower anchor 120.

Figure 4A:
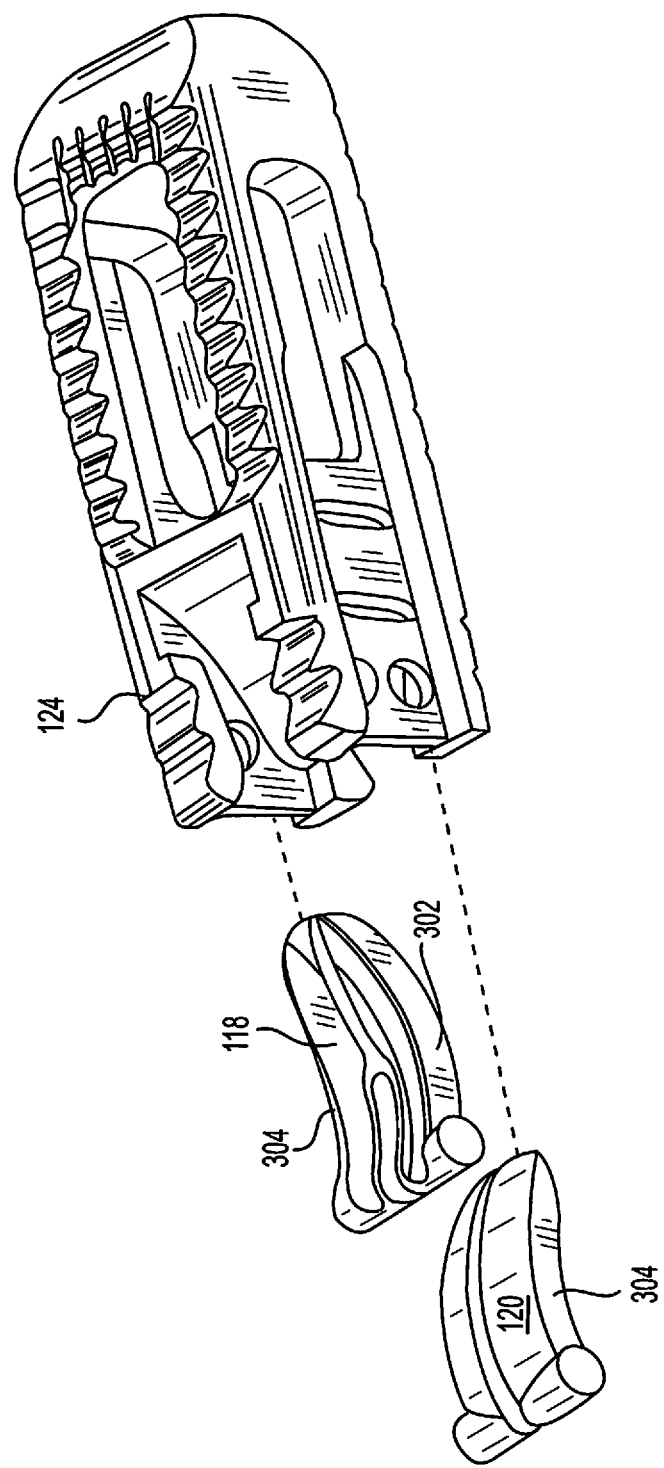
FIG. 4A depicts two anchors being loaded into the intervertebral spacer of FIGS. 1A and 1B.
Figure 4B:
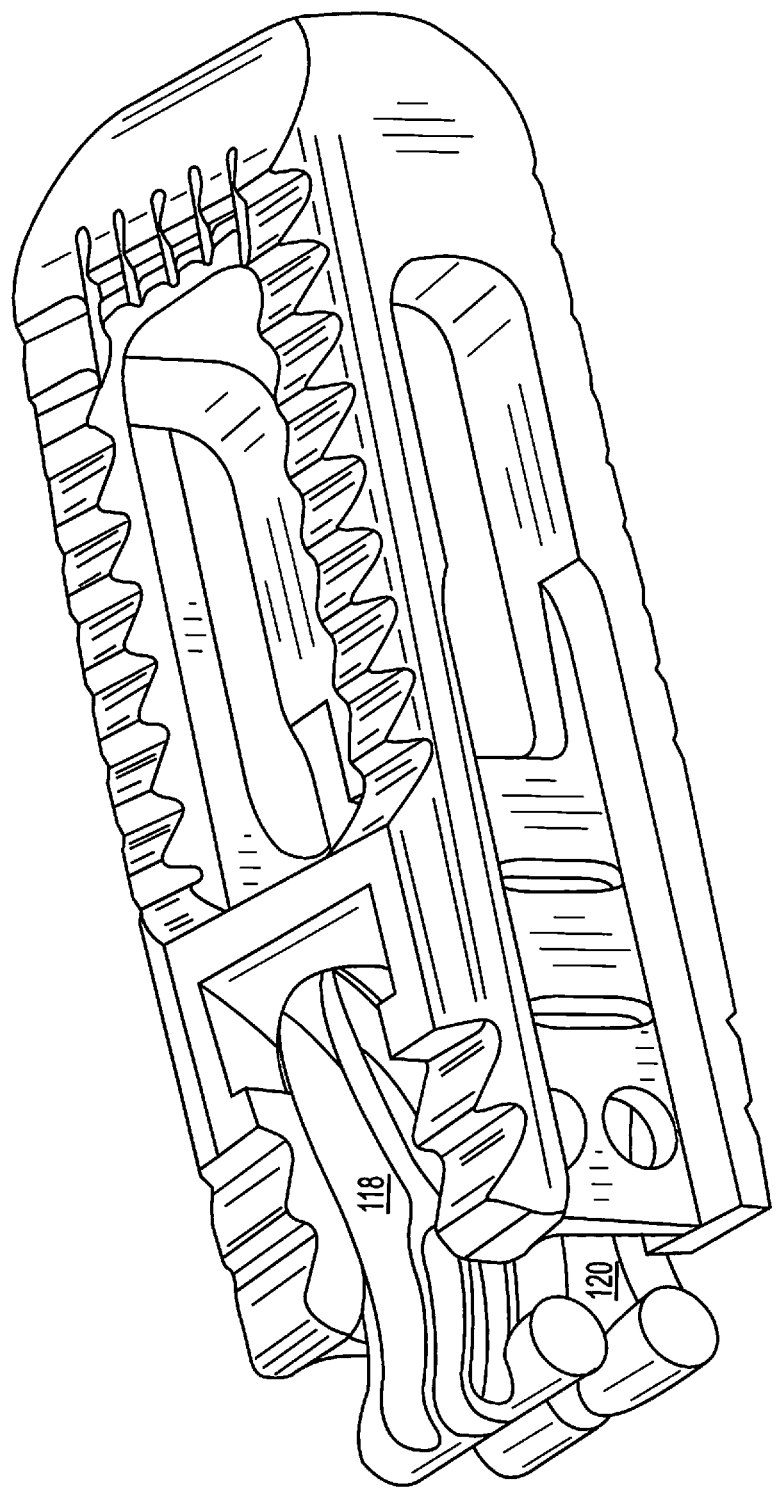
FIG. 4B depicts the two anchors of FIG. 4A loaded into the intervertebral spacer of FIGS. 1A and 1B, the two anchors being in an undeployed state.

FIG. 4A depicts upper anchor 118 and lower anchor 120 being loaded into spacer 100. As discussed above, the upper guide of spacer 100 has an upper pair of oppositely positioned lateral recesses 124. Each lateral recess 124 is adapted to receive a respective one of lateral sides 302 and 304 of upper anchor 118. Similarly, the lower guide of spacer 100 has a lower pair of oppositely positioned lateral recesses 128 (shown more clearly in FIG. 1B). Each lateral recess 128 is adapted to receive a respective one of lateral sides 302 and 304 of lower anchor 120. Turning now to FIG. 4B, this figure depicts spacer 100 loaded with the upper and lower anchors. In FIG. 4B, upper anchor 118 and lower anchor 120 are in an undeployed state and are disposed entirely within spacer 100. That is, no part of upper anchor 118 and lower anchor 120 extend beyond the profile of teeth 116 arranged on spacer 100. In the loaded/undeployed state, spacer 100 is ready to be gripped by an implantation instrument for simultaneous deployment into their respective intervertebral bodies.

Figure 5A:
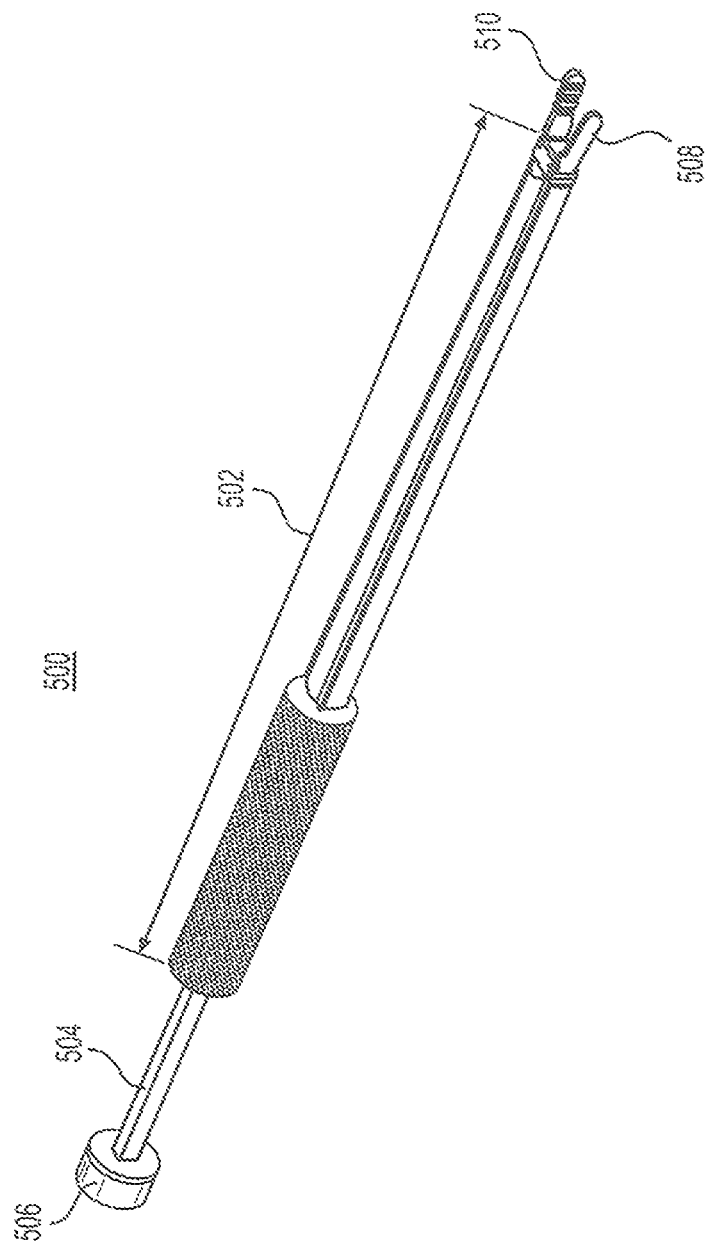
FIG. 5A depicts a perspective view of an implantation instrument in accordance with an illustrative embodiment of the present invention.

FIG. 5A is a perspective view of implantation instrument 500, which comprises, inter alia, housing 502, anchor driver 504, handle 506, and a pair of oppositely positioned grippers 508 and 510. As will be discussed in more detail below, with reference to FIGS. 5B-5D, anchor driver 504 can be advanced forwards or retracted backwards via handle 506 to respectively grip or release spacer 100.

Figure 5B:
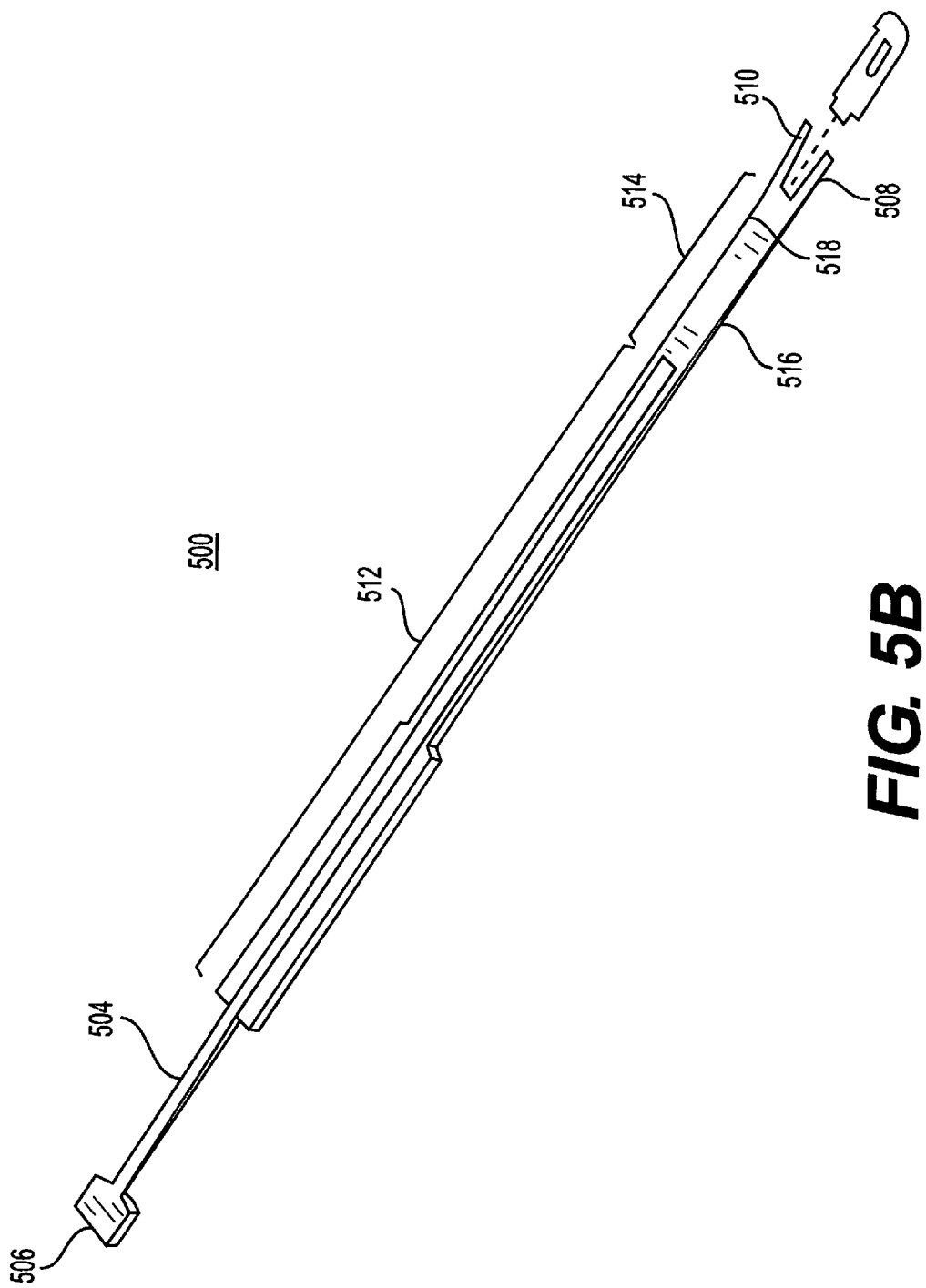
FIG. 5B depicts a cross-sectional view of the implantation instrument of FIG. 5A, the cross-sectional view depicting a narrower section and a wider section of the implantation instrument.

FIG. 5B is a cross-sectional view of the implantation instrument of FIG. 5A. As shown in this view, housing 502 is divided into two sections—namely, a narrower section 512 and a wider section 514. Anchor driver 504 is constructed to fit squarely into narrower section 512 with little or no lateral and radial movement, while the area of wider section 514 is dimensioned to accommodate the width of anchor driver 504 and a pair of adjacently positioned, oppositely bowed leaf springs 516 and 518.

In the configuration depicted in FIG. 5B, anchor driver 504 can be advanced forwards towards leaf springs 516 and 518 via handle 506. As the forward advancement causes anchor driver 504 to be wedged between leaf springs 516 and 518, their respective grippers 508 and 510 will begin to simultaneously pivot inward to clamp onto the lateral surfaces of spacer 100.

Figure 5C:
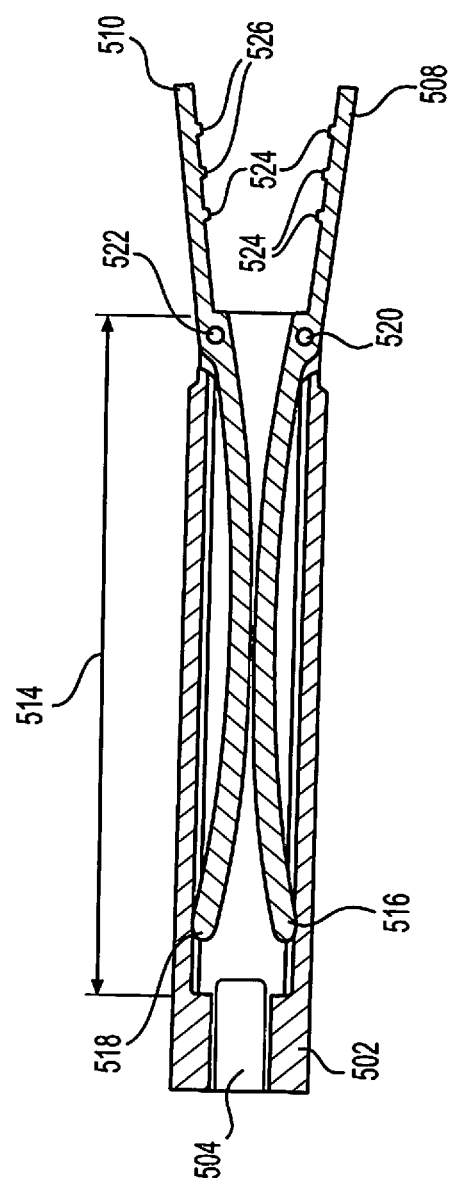
FIG. 5C depicts an exploded, cross-sectional view of the wider section of the implantation instrument of FIG. 5A.

More precisely, and with reference to FIG. 5C, the forward advancement of anchor driver 504 causes gripper 508 to pivot inwardly about pivot point 520. This pivot action is a result of leaf spring 516 being compressed outwards towards the wall of housing 502 as anchor driver 504 engages the bowed portion of leaf spring 516. As gripper 508 pivots inwards, ribs 524 engage their respective gripper recess 146 (depicted in FIG. 1A) arranged on spacer 100. Likewise, gripper 510 will pivot inwardly about pivot point 522 in response to the forward advancement of the driver, resulting in ribs 526 engaging their respective gripper recess 148 (depicted in FIG. 1B). By means of the foregoing, spacer 100 can be securely gripped by implantation instrument 500, as depicted in FIG. 5D.

Figure 5D:
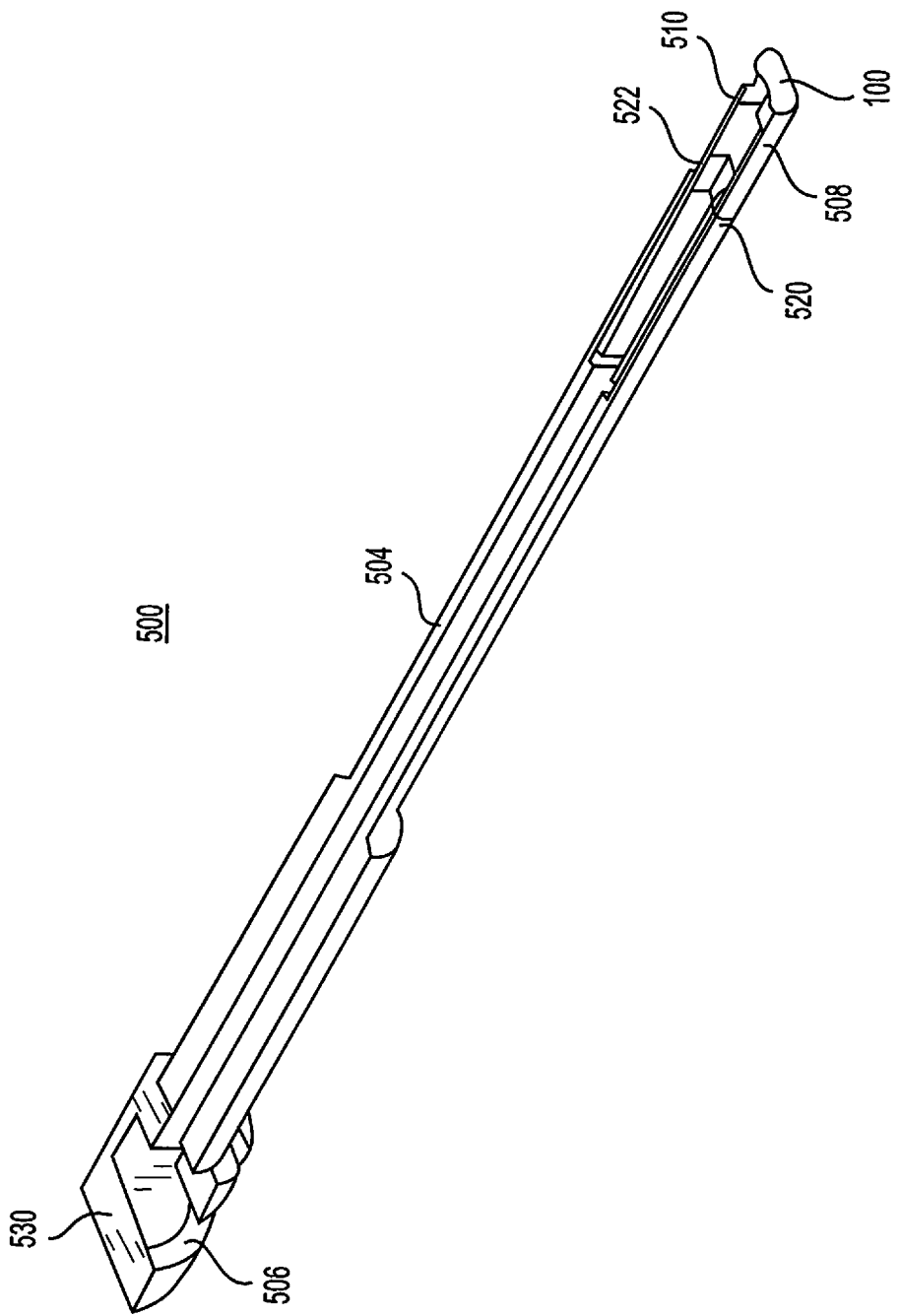
FIG. 5D depicts a cross-sectional view of the implantation instrument gripping the lateral surfaces of the intervertebral spacer of FIGS. 1A and 1B.

As depicted in FIG. 5D, the head of anchor driver 504 stops at or slightly before the distal end of housing 502 after gripping spacer 100. While spacer 100 is being gripped by implantation instrument 500, spacer 100 is positioned within the narrow disc space between adjacent vertebrae. Continuing to grip spacer 100 with implantation instrument 500, the surgeon removes cap 530 and is now ready to impact handle 506 with a weighted object (e.g., hammer, mallet, etc.). In accordance with the illustrative embodiment, cap 530 has two functionalities. First, cap 530 when attached to handle 506 disallows forward movement of anchor driver 504 past a certain point—namely, the distal end of housing 502. Secondly, cap 530 prevents inadvertent deployment of upper anchor 118 and lower anchor 120 during positioning of spacer 100 within the adjacent vertebral bodies.

When the surgeon impacts handle 506 with a weighted object, anchor driver 504 is driven forwards into the proximal portion of upper anchor 118 and lower anchor 120, thereby simultaneously deploying the anchors into their respective vertebrae. The surgeon may impact handle 506 one or more times so that the anchors reach a desired depth within their vertebrae, and so that the anchors engage the locking feature of the present invention described in more detail below. Once upper anchor 118 and lower anchor 120 is locked to spacer 100 in the deployed position, the surgeon can retract anchor driver 502 so that leaf springs 516 and 518 can return to their relaxed state. While returning to their relaxed state, grippers 508 and 510 will begin to pivot outwardly to disengage from their gripper recesses, thereby releasing spacer 100.

Figure 6A:
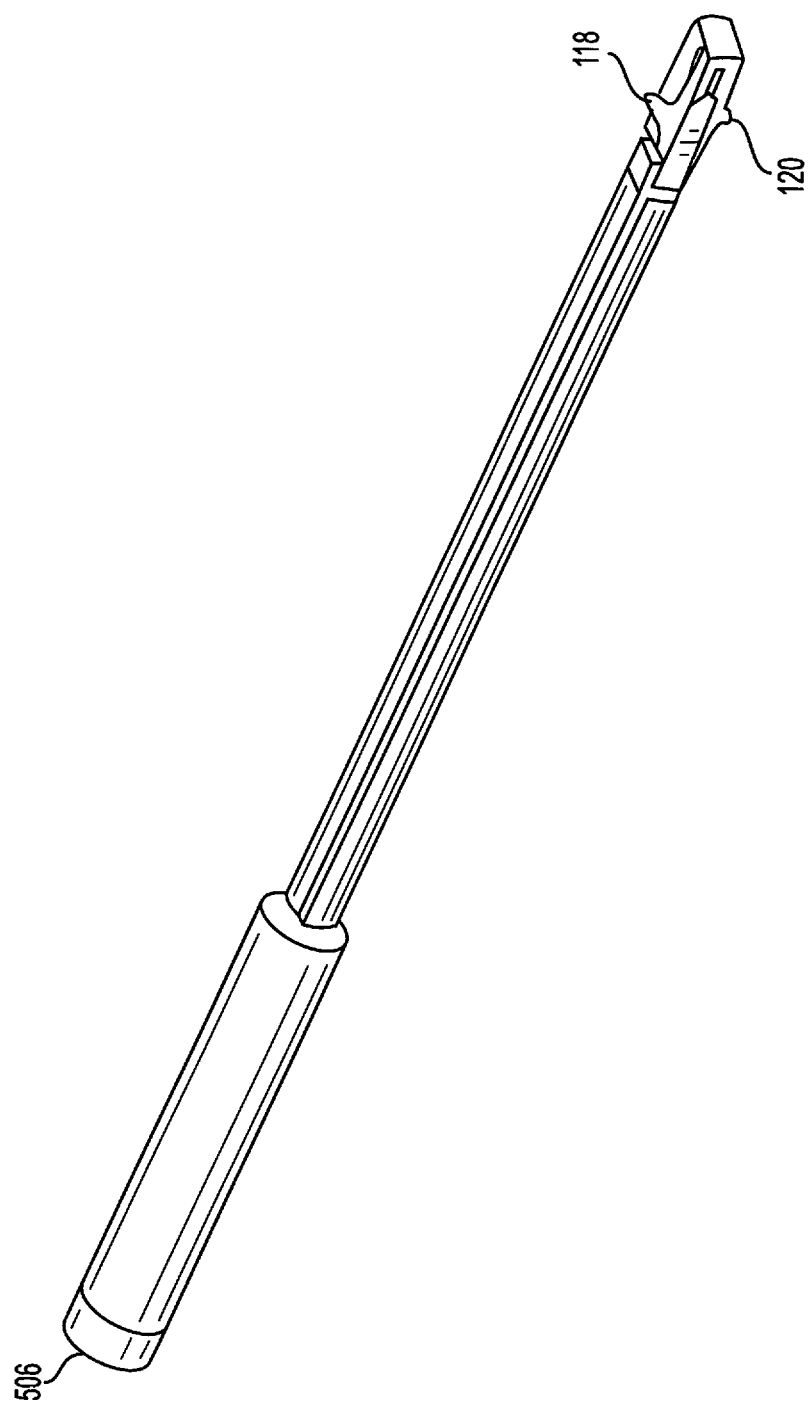
FIG. 6A depicts the implantation instrument of FIG. 5A having deployed the anchors of FIG. 4A.
Figure 6B:
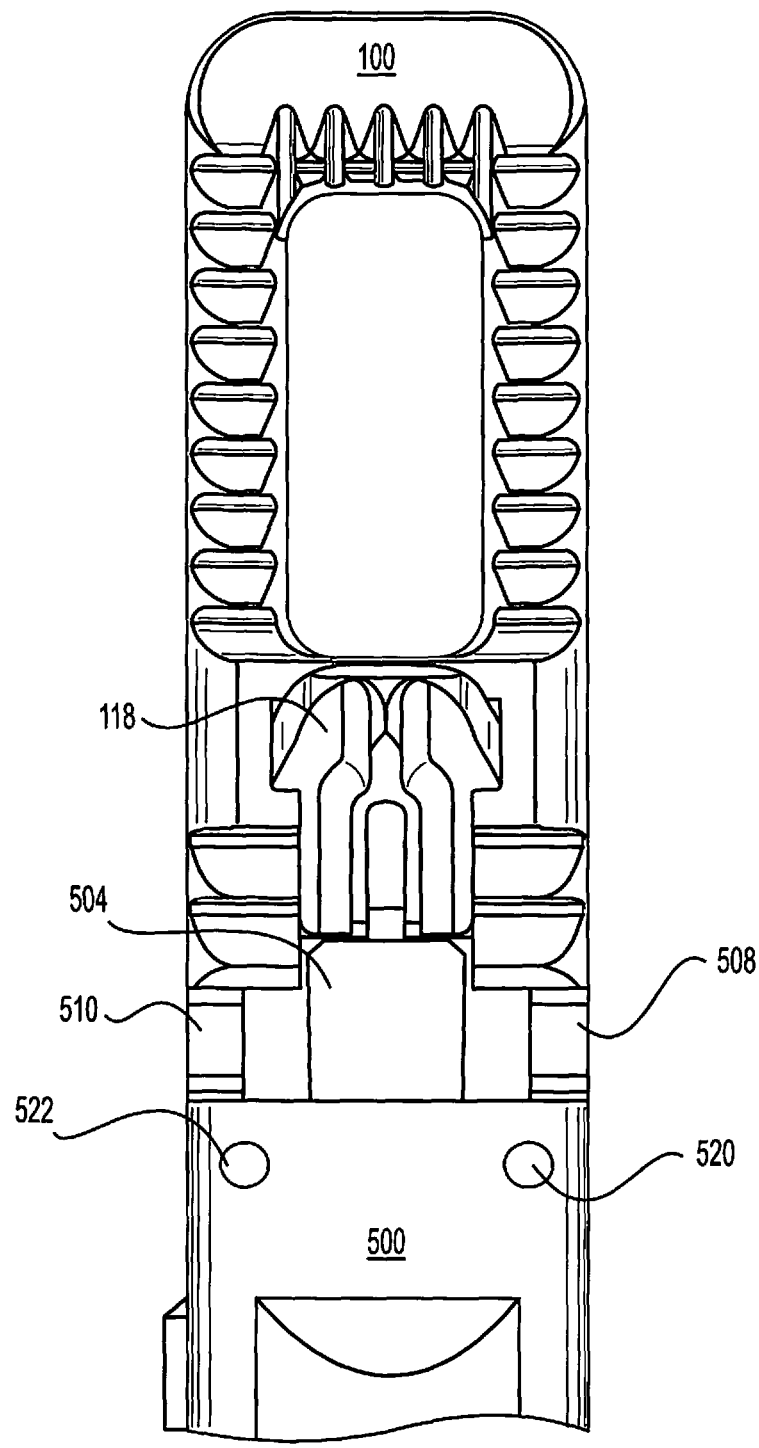
FIG. 6B depicts an exploded, top view of the deployed anchors of FIG. 6A.
Figure 6C:
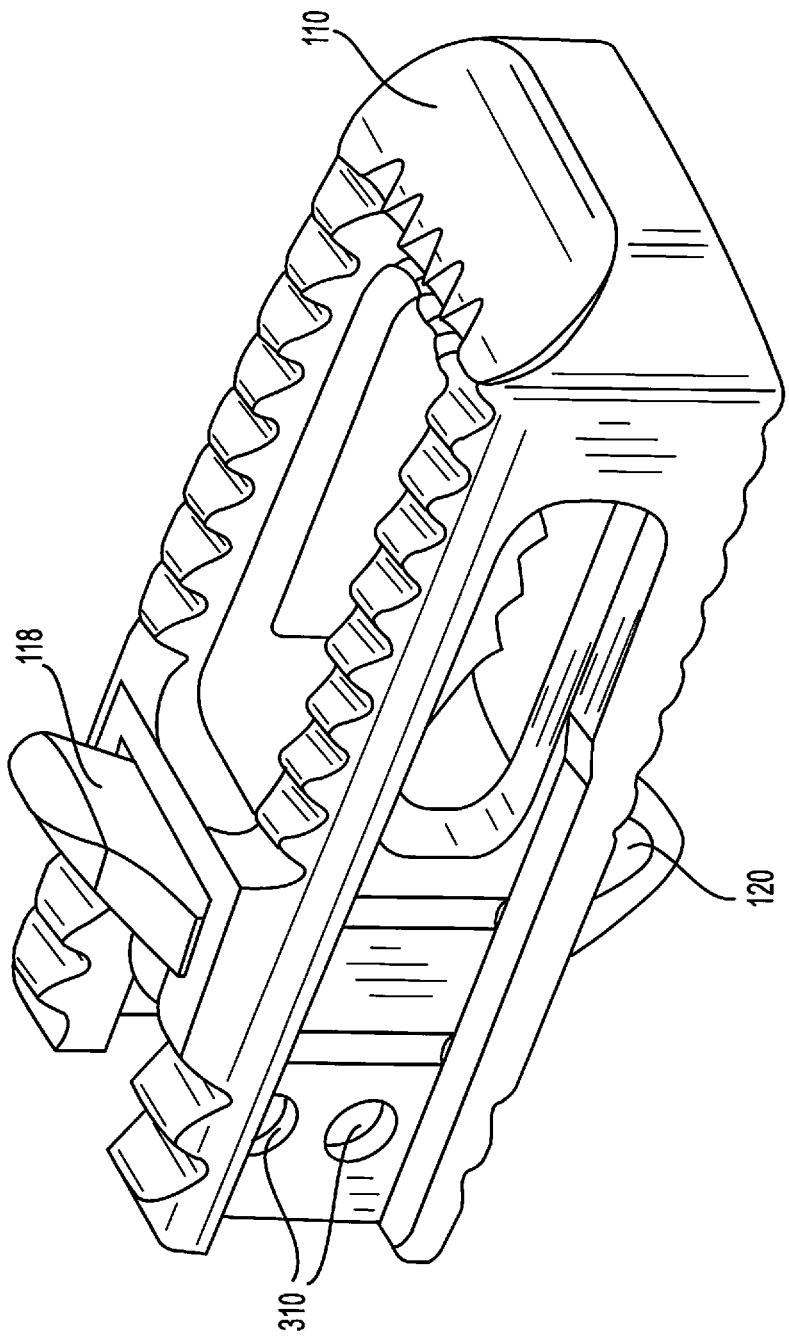
FIGS. 6C and 6D depict an exploded, perspective view of the deployed anchors of FIG. 6A.
Figure 6D:
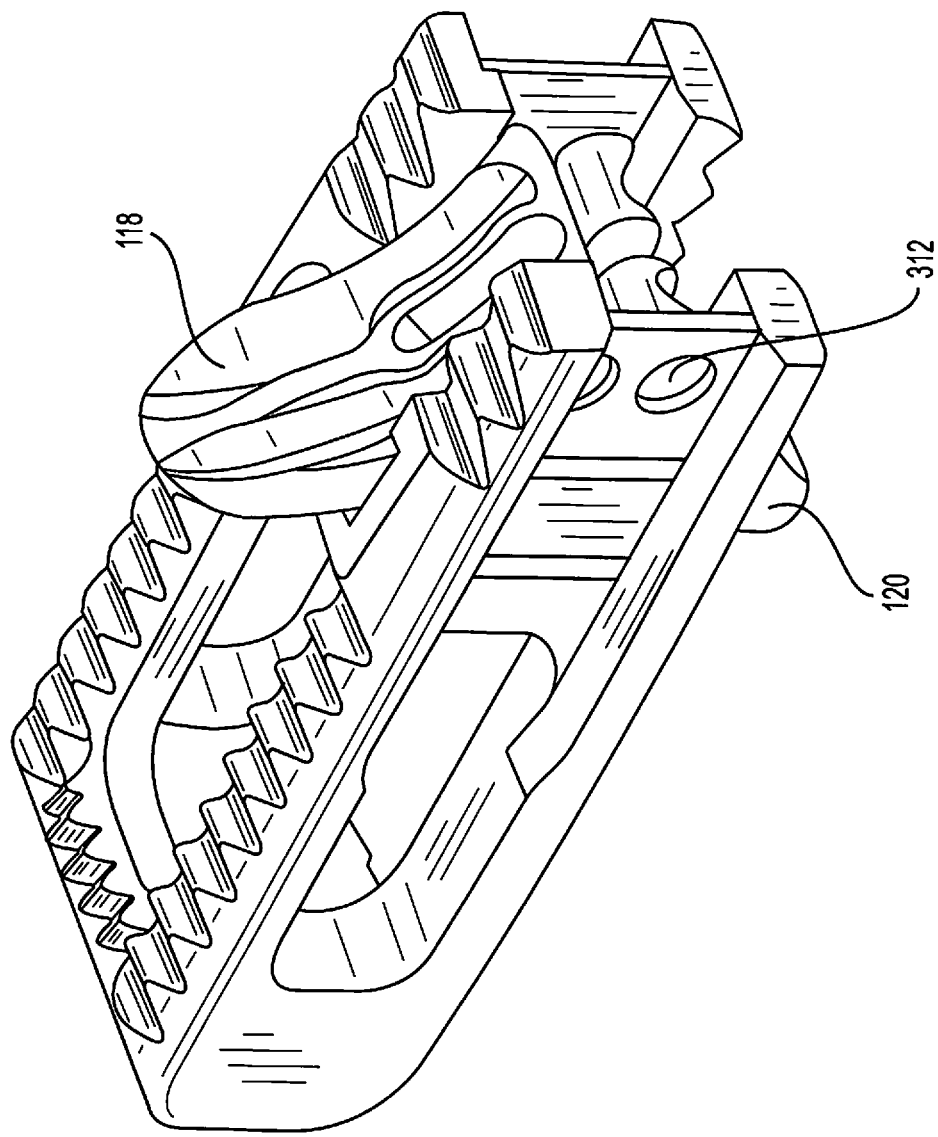

FIG. 6A depicts a perspective view of implantation instrument 500 in which driver anchor 504 has simultaneously deployed upper anchor 118 and lower anchor 120. As discussed above, the head of anchor driver 504 is simultaneously driven into the proximal portion of upper anchor 118 and lower anchor 120 as the surgeon impacts handle 506. This causes both the upper anchor 118 and lower anchor 120 to independently slide along the upper inclined surface 122 and lower inclined surface 126, respectively. The upper and lower inclined surfaces respectively press against the surface of the upper and lower anchors (i.e., the surface depicted in FIG. 3A) to deploy the anchors into their respective vertebral bodies. FIGS. 6B-6D depict upper anchor 118 and lower anchor 120 simultaneously deployed after being impacted by anchor driver 504. As shown in these figures, the distal ends of upper anchor 118 and lower anchor 120 in the deployed state are radially extended outside of spacer 100. That is, the distal ends of upper anchor 118 and lower anchor 120 extend past the height of teeth 116 of spacer 100 after being deployed.

From the foregoing discussion, it will be clear to those skilled in the art that upper anchor 118 and lower anchor 120 are separate elements that slide independently of each other along their respective upper and lower guides. It will also be clear from the foregoing discussion that an advantage of using the upper and lower anchors of the present invention is that they provide additional anchorage for stabilizing a spacer. In other words, not only is the spacer anchored to the intervertebral bodies via its teeth, the spacer is also provided with additional anchorage by the upper and lower anchors, since they extend past the profile of the teeth and therefore penetrating deeper into the intervertebral bodies.

Returning to FIGS. 6C and 6D, these figures depict upper anchor 118 and lower anchor 120 locked to spacer 100 in a deployed position. Since upper anchor 118 and lower anchor 120 are locked to spacer 100 in substantially the same way, the following discussion of FIGS. 6C and 6D will use the word "anchor" to describe both the upper and lower anchors.

As the anchor is impacted by driver 504, lateral projections 310 and 312 will respectively engage the sloping edge of lateral chamfers 130 and 132. Lateral chamfers 130 and 132 are depicted in the figures as being arranged proximally to locking recesses 134, 136, 138, and 140 of spacer 100. The pressure and force of the impact causes flexible prongs 306 and 308 to flex laterally inwardly. As lateral projections 310 and 312 past their respective lateral chamfers, flexible prongs 306 and 308 will return to a relaxed state, thereby causing lateral projections 310 and 312 to laterally extend into their corresponding locking recess 134, 136, 138, and 140. This locking feature of the present invention prevents the anchors from disengaging from spacer 100 after being deployed into the vertebral bodies.

Figure 7A:
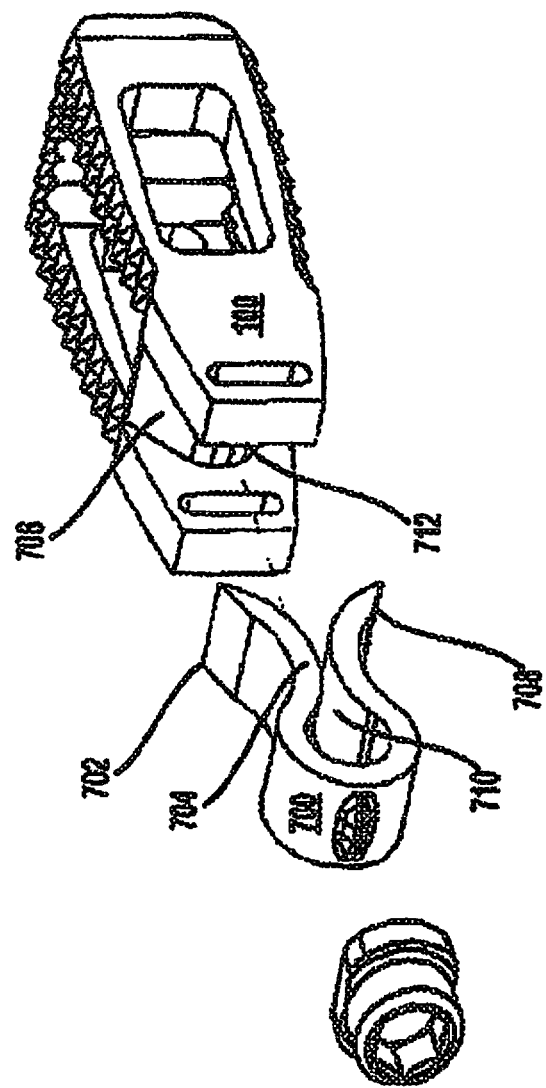
FIG. 7A-7C depict a spacer and anchor in accordance with an alternative embodiment of the present invention, wherein the upper and lower anchors of the anchoring device form a single, unitary piece.
Figure 7B:
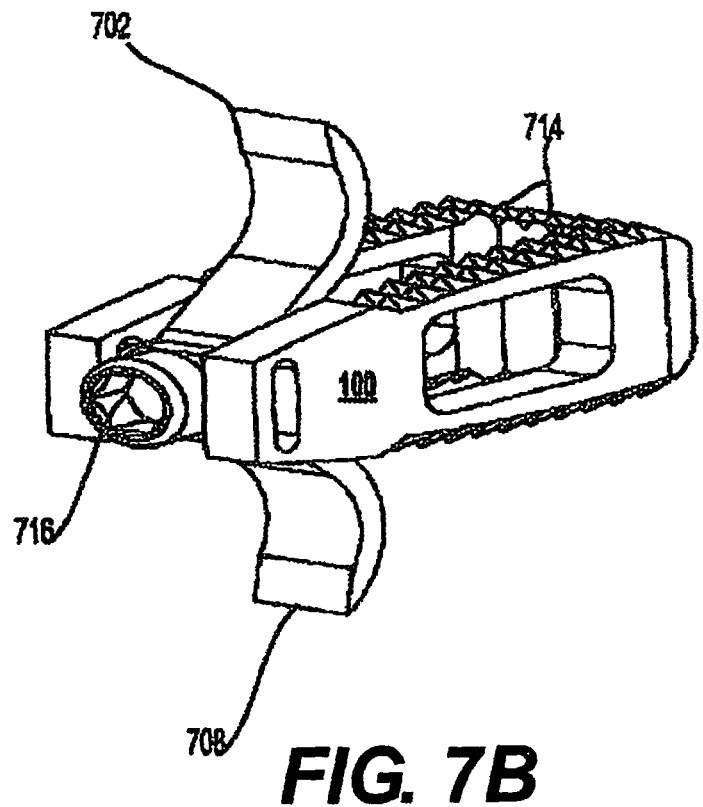
Figure 7C:
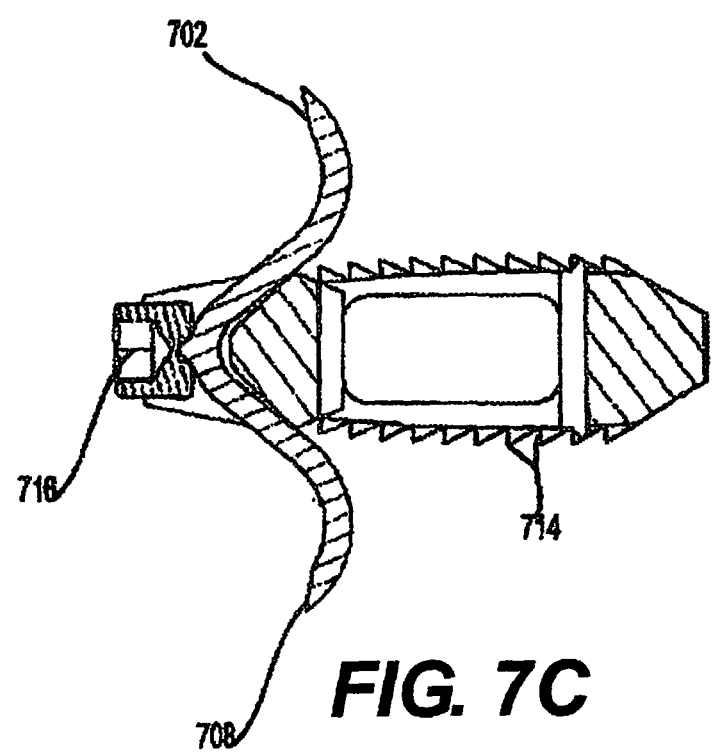

It will be clear to those skilled in the art, after reading this disclosure that numerous modification can be made to the illustrative embodiment without departing from the scope of the invention. For example, in one alternative embodiment, upper anchor 118 and lower anchor 120 can be constructed as a single unitary piece. FIGS. 7A-7C depict such an anchoring device.

As depicted in FIG. 7A, upper anchor 702 of anchoring device 700 comprises underside 704 that is adapted to press against upper inclined surface 706 of the upper guide arranged on spacer 100. Similarly, lower anchor 708 of anchoring device 700 comprises underside 710 that is adapted to press against lower inclined surface 712 of the lower guide arranged on spacer 100. As anchoring device 700 is advanced forwards, pressure causes the undersides to press against their respective inclined surfaces, which guides upper anchor 702 and lower anchor 708 to radially and simultaneously deploy into their respective vertebral bodies. As depicted in FIGS. 7B and 7C, upper anchor 702 and lower anchor 708 extend past the profile of teeth 714 to provide additional anchorage. Once the upper and lower anchors have been simultaneously deployed into their vertebra, locking cap 716 can be used to lock the anchors in their deployed position. Specifically, locking cap 716 is adapted to press the proximal end of anchoring device 700 to lock the anchoring device to spacer 100.

Figure 8A:
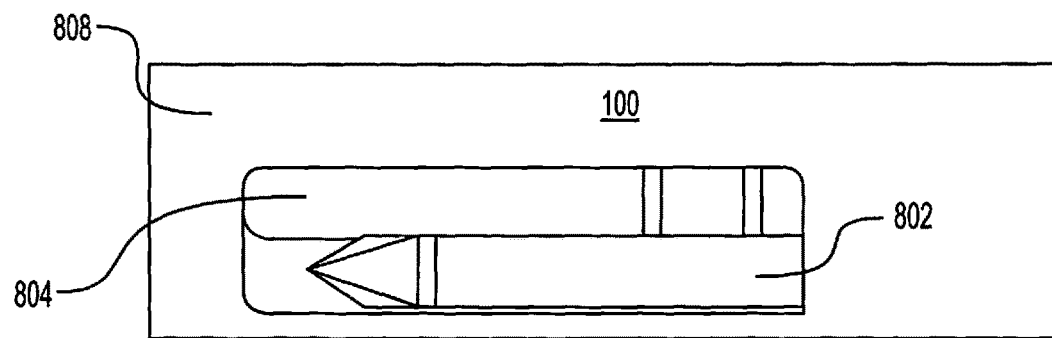
FIG. 8A-8C depict a spacer and anchor in accordance with an alternative embodiment of the present invention, wherein the upper and lower anchors of the anchoring device are disposed entirely within the spacer.
Figure 8B:
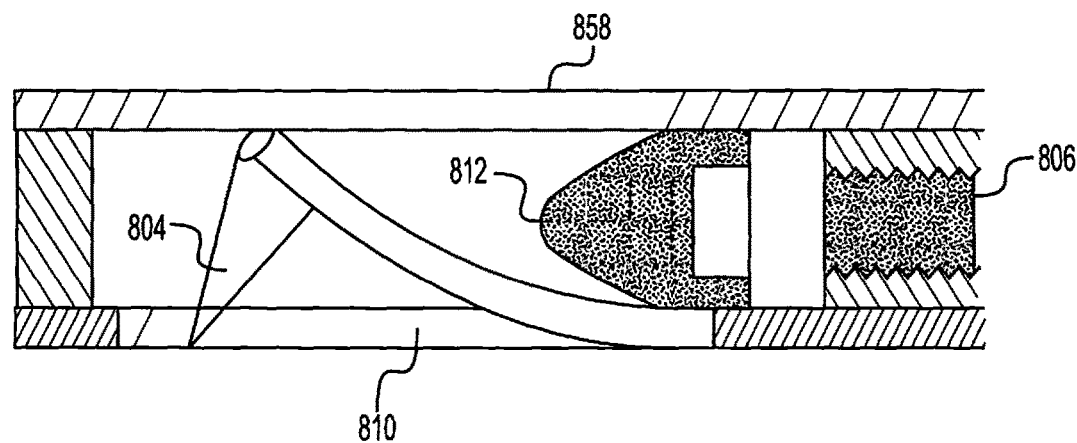
Figure 8C:
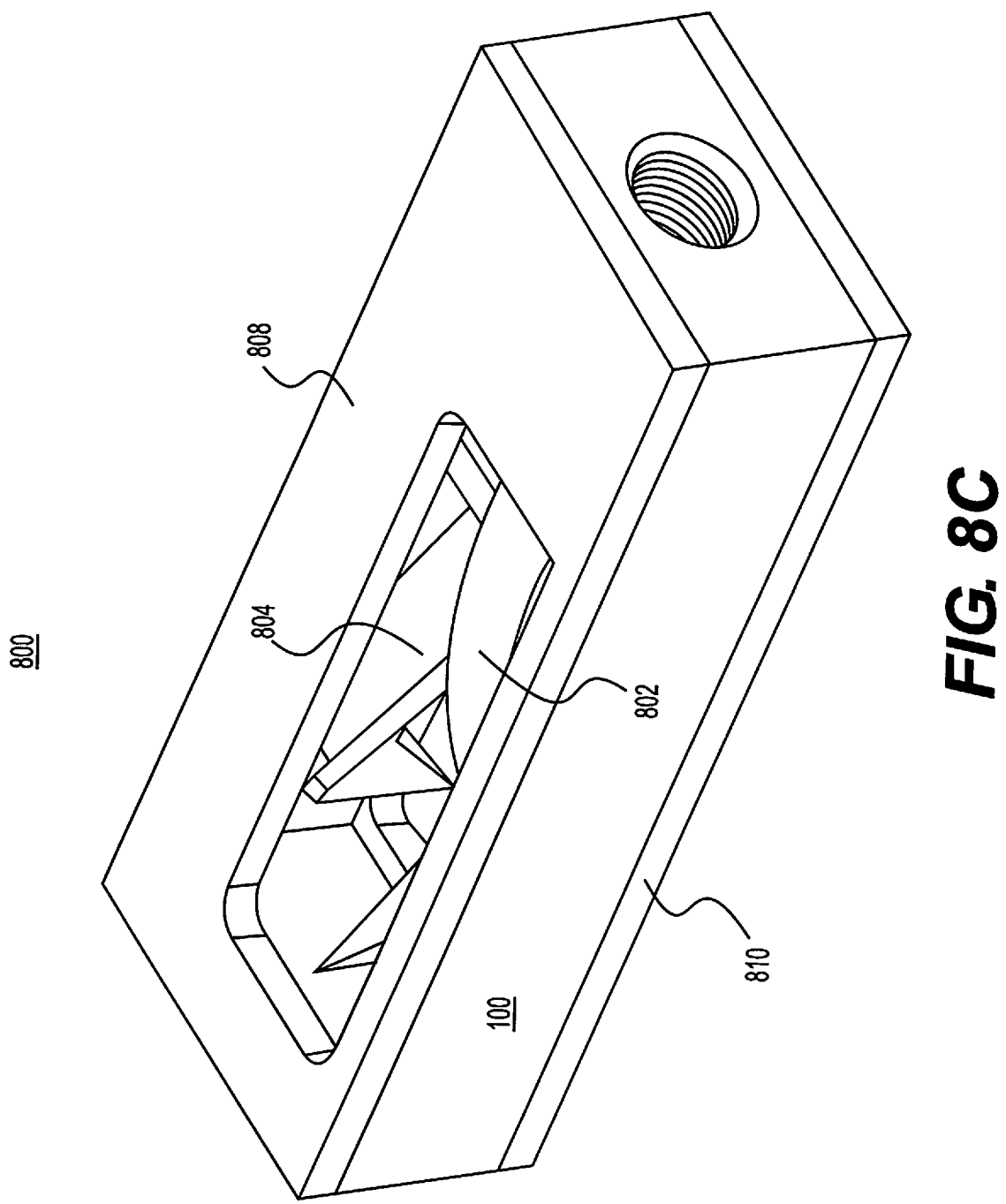

In another embodiment, as depicted in FIGS. 8A-8C, spacer 100 houses both upper anchor 802 and lower anchor 804. In other words, both the upper and lower anchors are disposed entirely within spacer 100 when the anchors are in a relaxed state. As shown in FIG. 8B, an internal drive screw 806 (i.e., an anchor drive) can be turned so that wedge 812 can be advanced forwards towards the bowed portion of both upper anchor 802 and lower anchor 804. Wedge 812 is forcibly advanced towards the bowed portion to simultaneously force upper anchor 802 and lower anchor 804 to extend through an opening arranged on superior surface 808 and inferior surface 810 of spacer 100. More precisely, as drive screw 806 is turned, wedge 812 abuts against the bowed portion of upper anchor 802 and lower anchor 804. As wedge 812 abuts against the bowed portion of the anchors, the inclined surface of wedge 810 slides along the surface of upper anchor 802 and lower anchor 804. The sliding motion applies pressure to the surfaces of the anchors, thereby forcing both upper anchor 802 and lower anchor 804 to radially extend outside of the openings of spacer 100 and into their respective intervertebral bodies.

In a further embodiment, as depicted in FIGS. 9A-9H, the anchoring device has a drive plate 906 from which upper anchor 902 and lower anchor 904 extend.

Figure 9A:
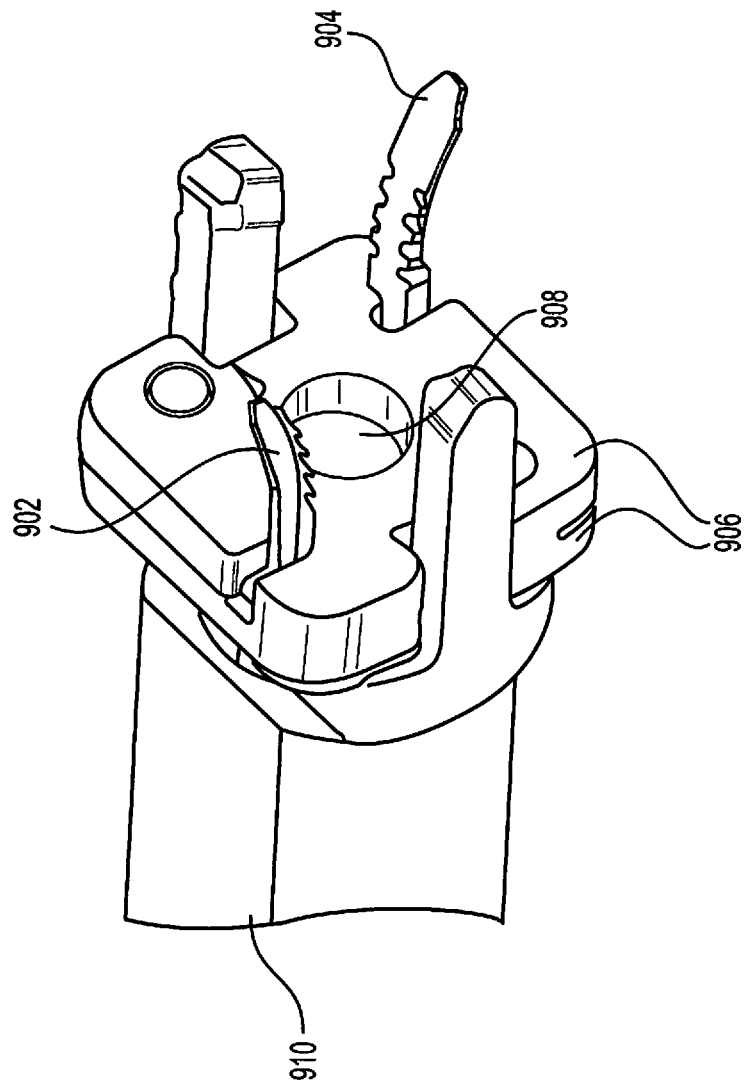
FIG. 9A-9H depict an upper anchor and a lower anchor arranged on a drive plate in accordance with an alternative embodiment of the present invention.

The drive plate of FIG. 9A includes through-hole 908 arranged at its central axis. The drive plate can be divided into four quadrants, with through-hole 908 being the origin point, like in a two-dimensional Cartesian plane. Upper anchor 902 extends from a first one of the quadrants (e.g., Quadrant I in a two-dimensional Cartesian plane), while lower anchor 904 extends from a second one of the quadrants (e.g., Quadrant III in the two-dimensional Cartesian plane), wherein the first and second quadrants are diagonally located from each other on drive plate 906. Although the anchors have been described as having a specific arrangement on drive plate 906, it will be clear to those skilled in the art after reading this disclosure that upper anchor 902 and lower anchor 904 can be arranged anywhere on the drive plate without departing from the scope of the present invention.

As further depicted in FIG. 9A, each of upper anchor 902 and lower anchor 906 has a pointed tip and a plurality of projections arranged on their lateral surfaces. The plurality of projections can be, for example, and without limitation, barbs that are angled away from the point in which the anchors penetrate into their respective vertebrae. The barbs are advantageous because they make it difficult for the anchors to come loose, thus ensuring that the spacer is securely stabilized between the vertebrae after implantation. FIG. 9A also depicts a pair of oppositely positioned grippers of holder 910 gripping onto the lateral surfaces of drive plate 906.

Figure 9B:
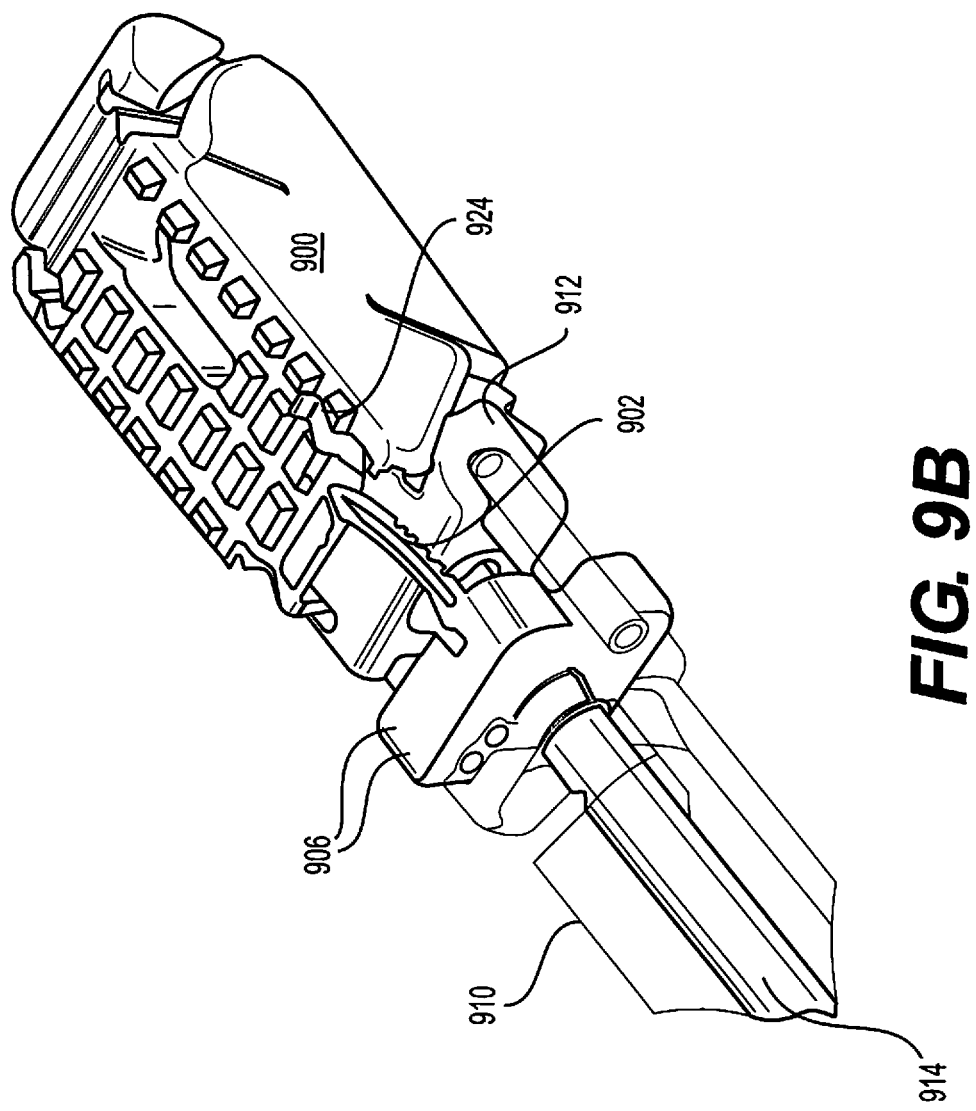
Figure 9C:
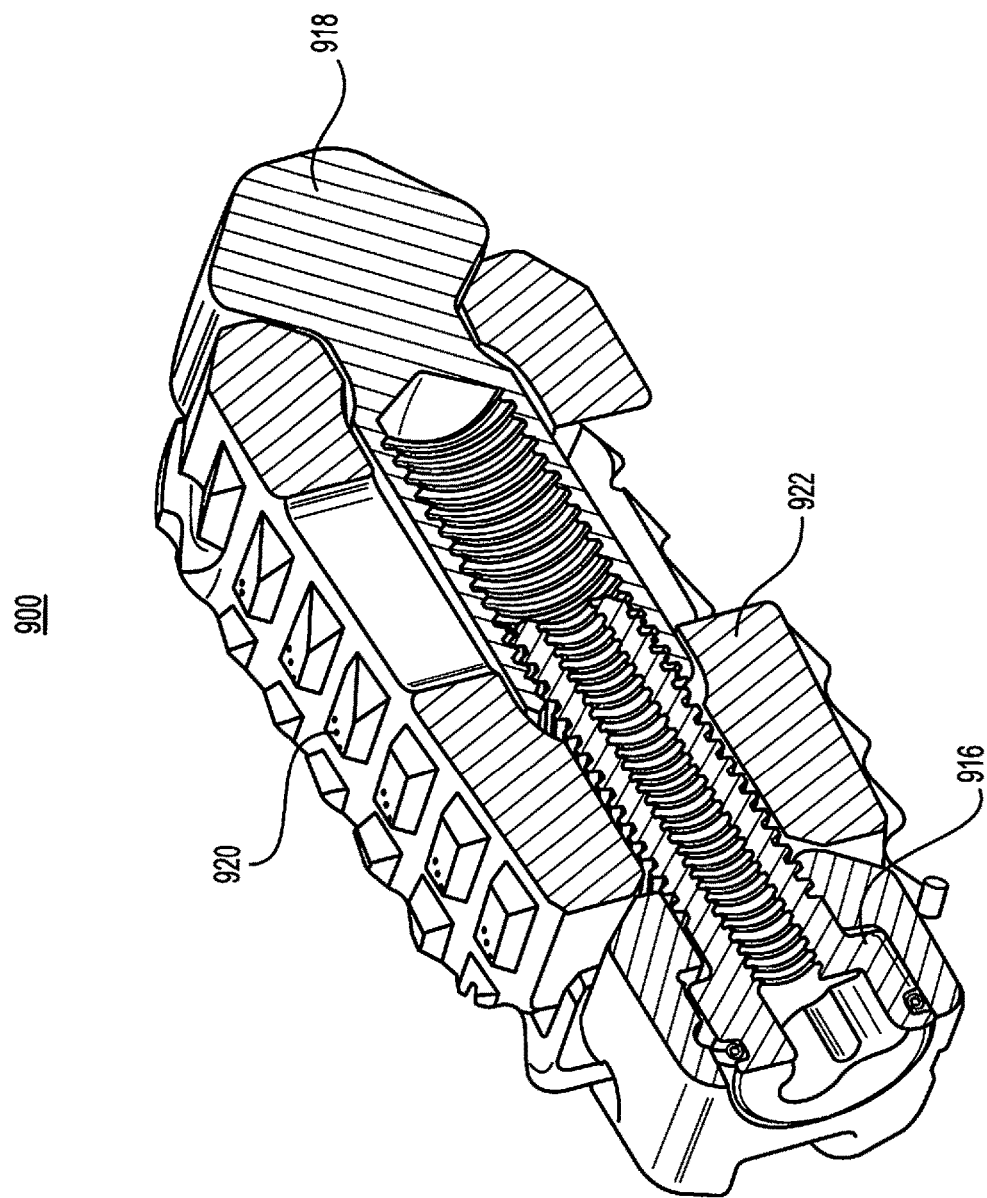
Figure 9D:
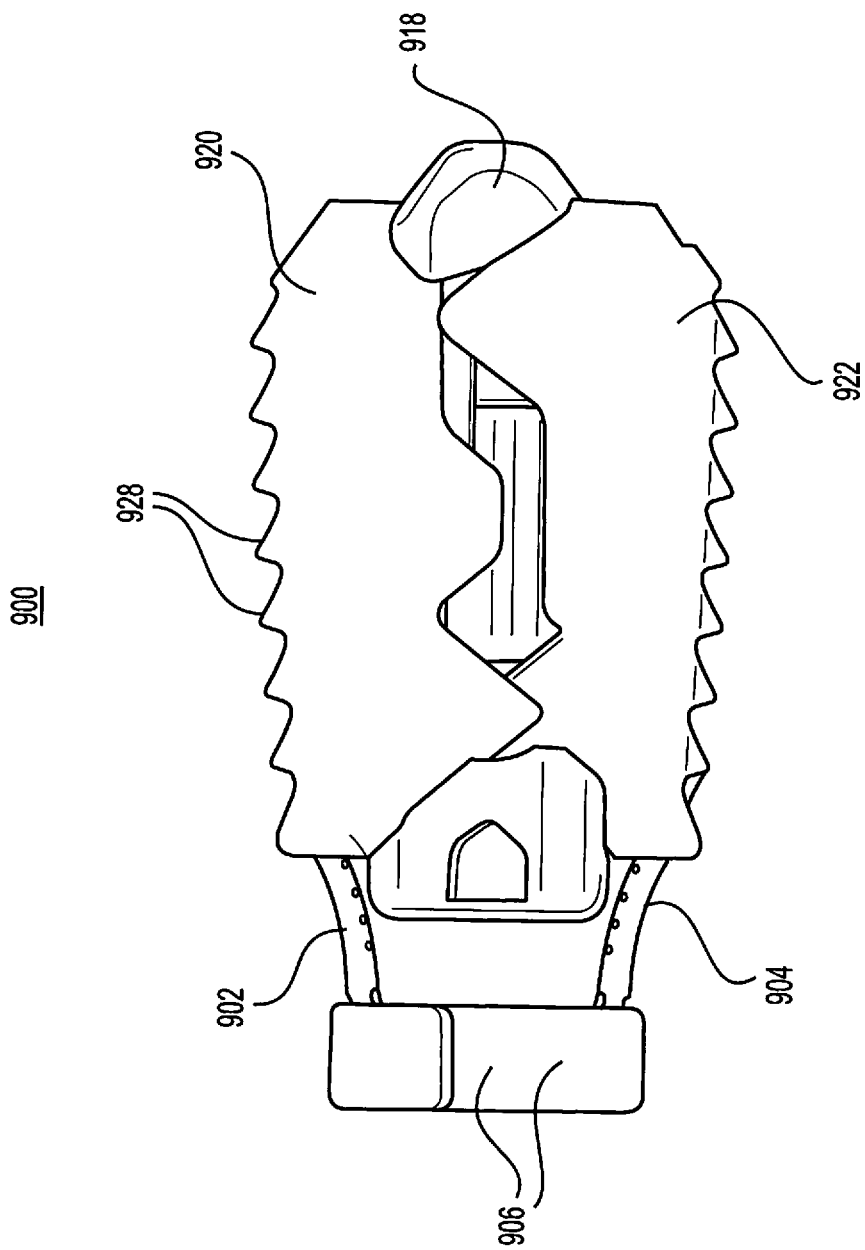

Turning now to FIG. 9B, while drive plate 906 is gripped by holder 910, a surgeon can position the grippers of holder 910 to also grip onto endplate 912 of spacer 900. Once endplate 912 is gripped by the surgeon, a driver 914 can be inserted into holder 910, which passes through through-hole 908 of drive plate 906. The driver engages one end of drive screw 916 (shown in FIG. 9C) housed within spacer 900. Once the driver has engaged the drive screw, the surgeon can turn driver 914 so that drive screw 916 can be threaded into the body of wedge 918. This causes wedge 918 to move backwards towards the proximal end of spacer 900, which in turn causes superior surface 920 and inferior surface 922 of the spacer to slide along the inclined surface of wedge 918. This can be seen more clearly in FIGS. 9C and 9D. As superior surface 920 and inferior surface 922 radially extend in opposite directions of each other, upper anchor 902 and lower anchor 904 engage upper guide 924 and lower guide 926 of spacer 900. As shown in FIG. 9D, the tips of upper anchor 902 and lower anchor 904 do not extend past the profile of teeth 928 of spacer 900, even after superior surface 920 and inferior surface 922 have been fully extended.

Figure 9E:
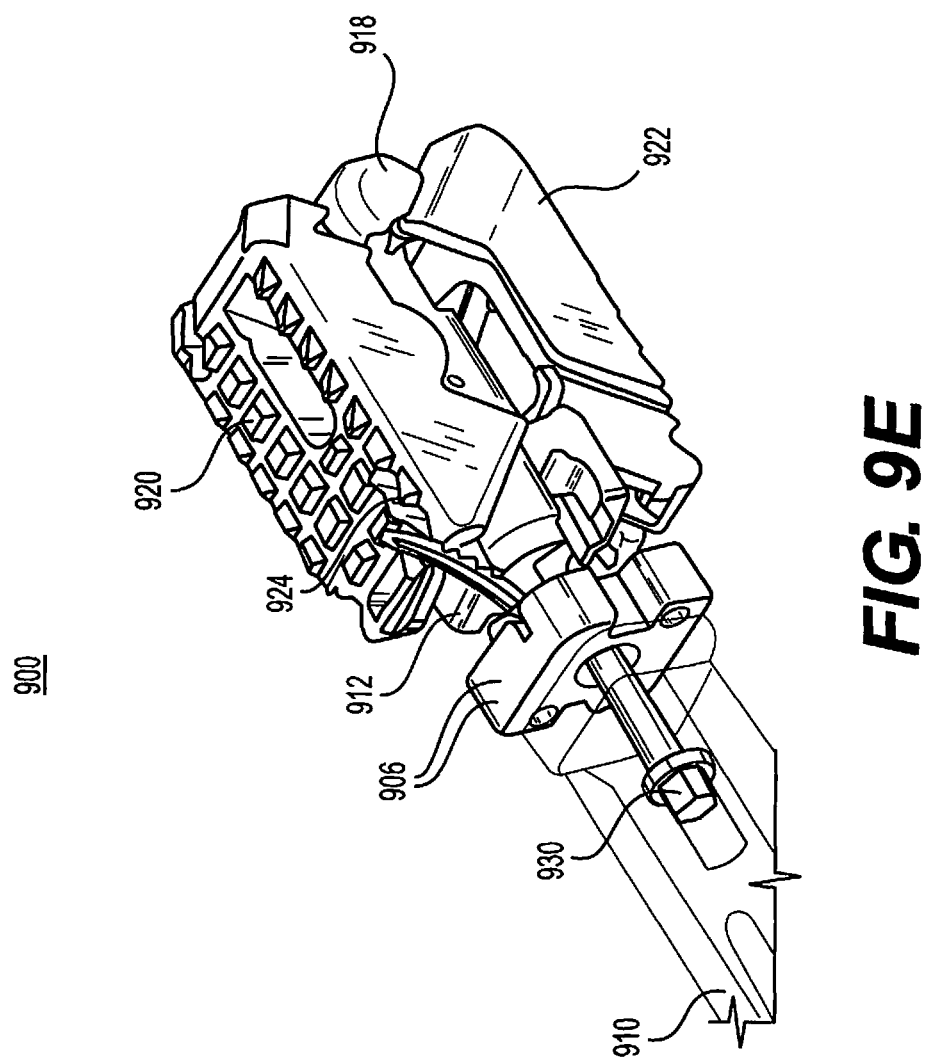
Figure 9F:
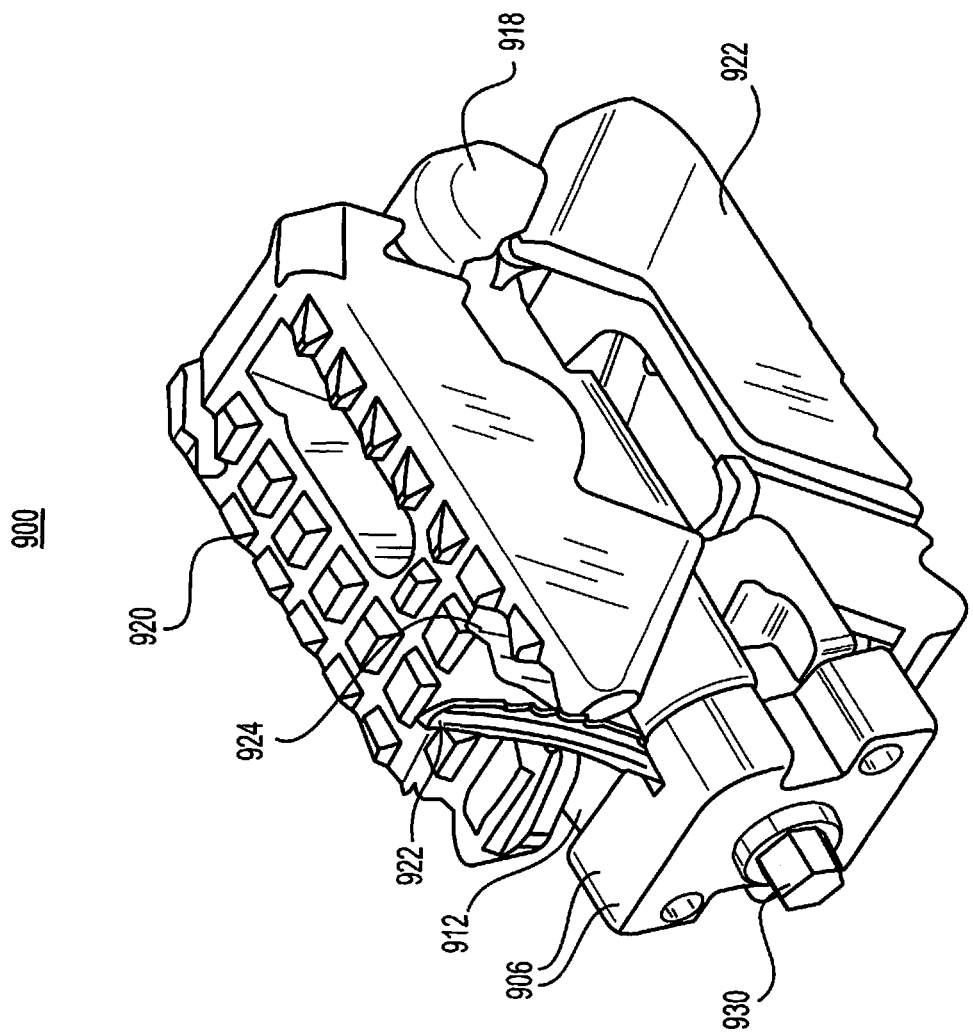
Figure 9G:
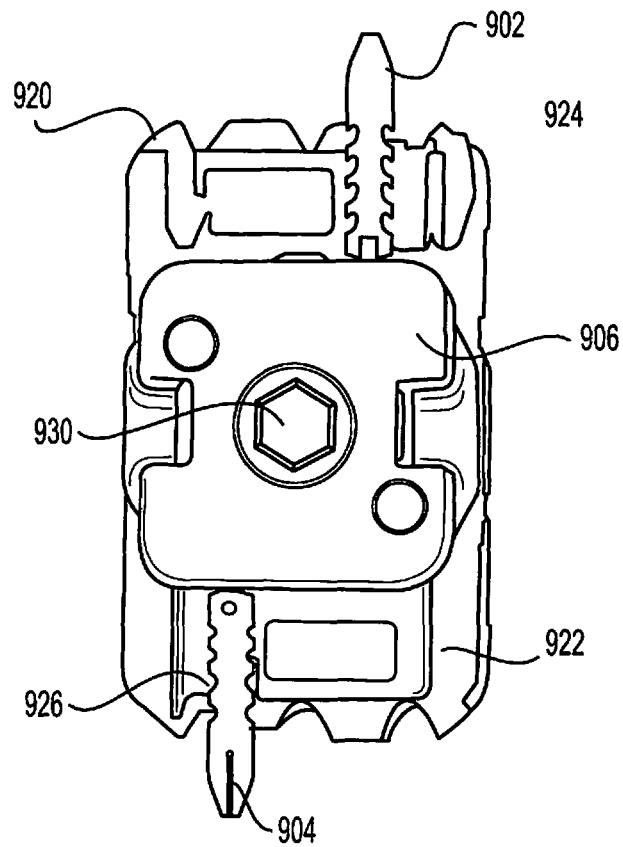
Figure 9H:
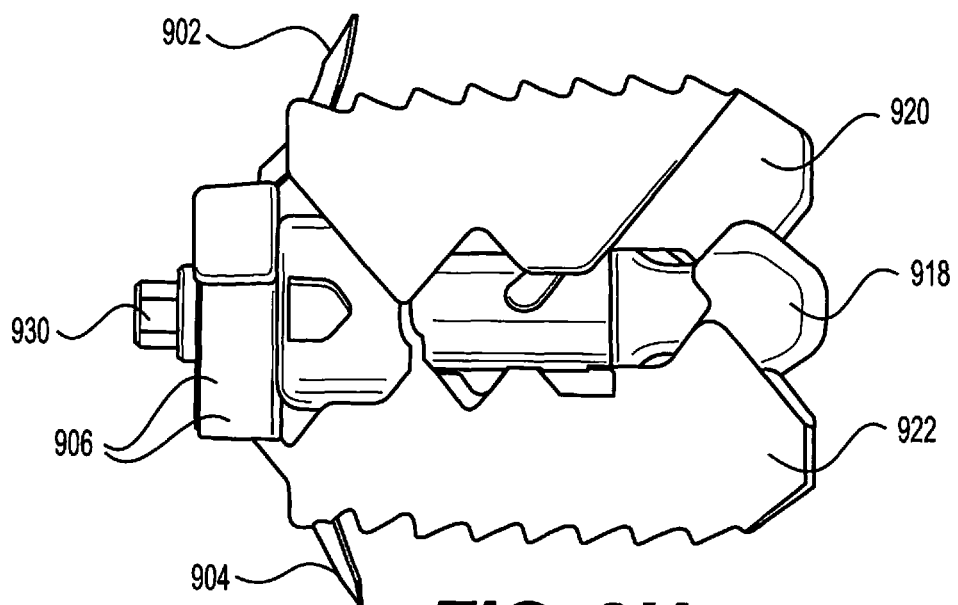

Once the superior and inferior surfaces of spacer 900 have been fully extended, the surgeon can now retract driver 914 and insert pull screw 930 (i.e., anchor driver) as shown in FIG. 9E. Pull screw 930 is physically adapted to be inserted through through-hole 908 and into the threaded hole of drive screw 916. Pull screw 930 can now be threaded to advance drive plate 906 towards the proximal end of spacer 900, which causes upper anchor 902 and lower anchor 904 to respectively slide along upper guide 924 and lower guide 926 as the drive plate is advanced towards the proximal end of the spacer. As upper anchor 902 and lower anchor 904 slide along their respective guides, the anchors simultaneously and radially extend away from spacer 900 and into their respective intervertebral bodies. Pull screw 930 is threaded by the surgeon until drive plate 906 is fully seated against endplate 912. Not only does threading pull screw 930 in this way fully deploy the anchors into their respective intervertebral bodies, it also locks the anchors to spacer 900 in a deployed position, as shown in FIGS. 9F-9H.

Figure 10:
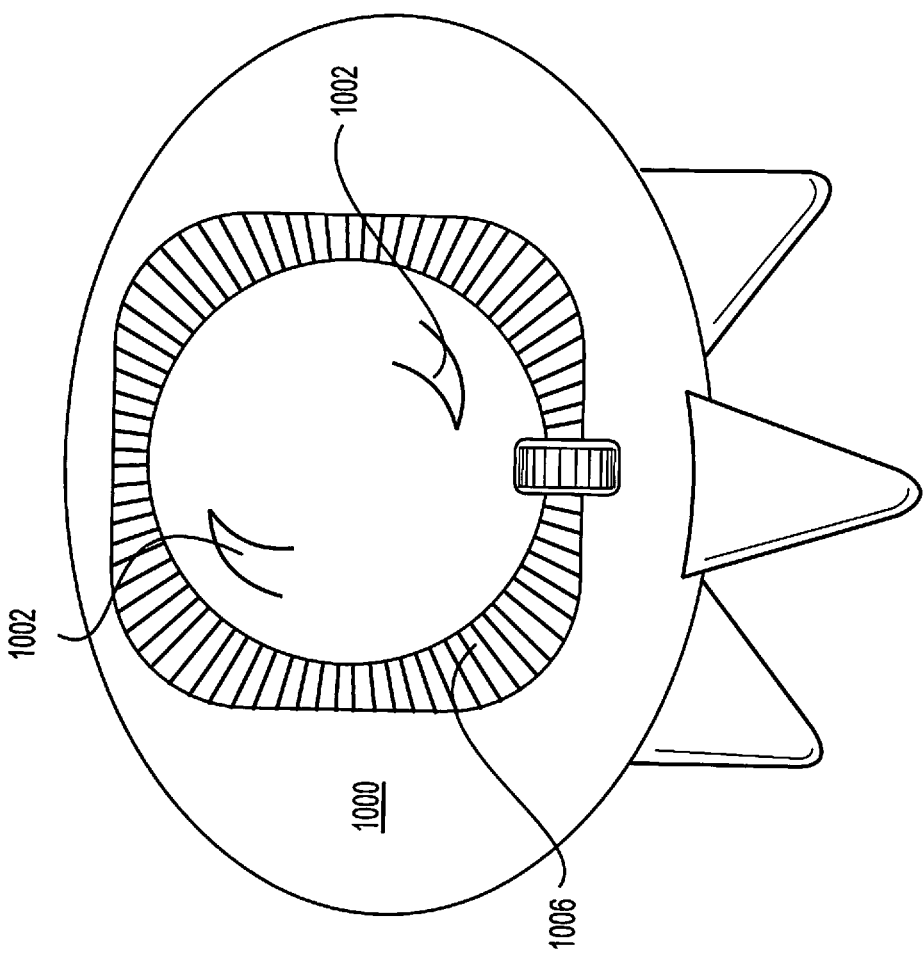
FIG. 10 depicts a spacer having worm gear for deploying one or more anchors in accordance with an alternative embodiment of the present invention.

FIG. 10 depicts a spacer-anchor combination in accordance with an alternative embodiment of the present invention. More specifically, the figure depicts spacer 1000, a plurality of upper anchors 1002, worm 1004, and gear 1006. In accordance with this embodiment, the worm is physically adapted to turn the gear, but the gear cannot turn the worm. This is because the angle on the worm is so shallow that, when the gear tries to spin it, the friction between the gear and the worm holds the worm in place. With this in mind, a surgeon can implant spacer 1000 in the disc space of adjacent vertebrae. The surgeon can then use a tool to turn worm 1004 in order to rotate gear 1006 in a particular direction. As the gear rotates, upper anchors 1002 are simultaneously deployed into an intervertebral body. Once deployed, pressure from adjacent vertebrae compressing down onto gear 1006 will not cause the gear to rotate. This is because, as discussed above, the angle on the worm is so shallow that the friction between the gear and the worm essentially locks the worm in place. Accordingly, upper anchors 1002 will be locked in their deployed position until worm 1004 is operated.

An alternative embodiment of a spacer-anchor combination 200 ("spacer 200") that may be used as an intervertebral fusion device is shown in FIGS. 11-18. As depicted in FIGS. 11-14, spacer 200 comprises a spacer body 201 having a superior surface 202, an opposing inferior surface 204, a pair of generally parallel lateral side surfaces 206 and 208, a distal end portion 210, and a proximal end portion 212 extending between superior surface 202 and inferior surface 204. Lateral side surfaces 206 and 208 extend between distal end portion 210 and proximal end portion 212. Inferior surface 204 is a mirror image of superior surface 202 across a plane "P" that bisects body 201 between superior surface 202 and inferior surface 204. Plane P extends perpendicularly from the plane of the paper of FIG. 13. Additionally, lateral surface 208 is a mirror image of lateral side surface 206.

An interior space 214 is provided inside spacer 200 that is open and accessible through each of superior surface 202, inferior surface 204, and lateral side surfaces 206, 208. In particular, the lateral side surfaces 206, 208 may each include an enlarged opening 205. The enlarged openings 205 may be generally rectangular in shape with rounded corners. For example, the enlarged openings 205 may be configured to each have a width greater than a height of the opening 205 such that the enlarged opening 205 generally spans along a longitudinal length of the spacer 200. Interior space 214 can be filled with a graft material (not shown) and used to encourage bone growth into spacer 200 to further secure spacer 200 after implantation.

Lateral side surface 206, 208 may also each include a recess 209 defined therein. Each of the recesses 209 may be positioned proximate to the proximal end portion 212 of the spacer 200. The recesses 209 may be sized and dimensioned to be gripped by an instrument, such as an inserter configured to implant the spacer 200 between adjacent vertebrae. The recesses 209 preferably have a semi-spherical or hemispheric configuration with a rounded edge positioned more distally and terminating in two elongated flat edges proximate to the superior and inferior surfaces 202, 204. The hemispheric recesses 209 preferably have a height at least equivalent to or greater than the height of the enlarged openings 205 in the side surfaces 206, 208 of the spacer 200.

As previously described, surfaces 202 and 204 may include a plurality of protrusions, ridges, or teeth 216 to help prevent spacer 100 from expulsion after being implanted between the adjacent vertebrae. The teeth 216 may extend between the lateral side surface 206, 208 and generally between the distal and proximal end portions 210, 212. Preferably the superior and inferior surfaces 202, 204 include at least one tooth 216 or a plurality of teeth 216 positioned behind each of the anchors 218, 220. In other words, one or more teeth 216 should be positioned between the anchor 218, 220 and the proximal end portion 212 of the spacer 200. These teeth 216 preferably extend from lateral side surface 206 to lateral side surface 208. The teeth 216 may include one or more indentations 217 which interrupt the teeth 216. The indentations 217 may run generally perpendicular to the teeth 216 and may extend from proximal end portion 212 towards the exits of passages 230, 232 on the superior and inferior surfaces 202, 204.

Spacer 200 can be formed from titanium, titanium alloys, or other biocompatible materials. For example, polyetheretherketone (PEEK), other surgical grade metals, alloys, or a combination thereof can also be used to form spacer 200.

Beginning at distal portion 210, spacer 200 is constructed to have a tapered end 211 that narrows towards the distal most end. This design helps facilitate easier entry of spacer 200 into the narrow disc space arranged between two adjacent vertebral bodies (not shown).

Figure 13:
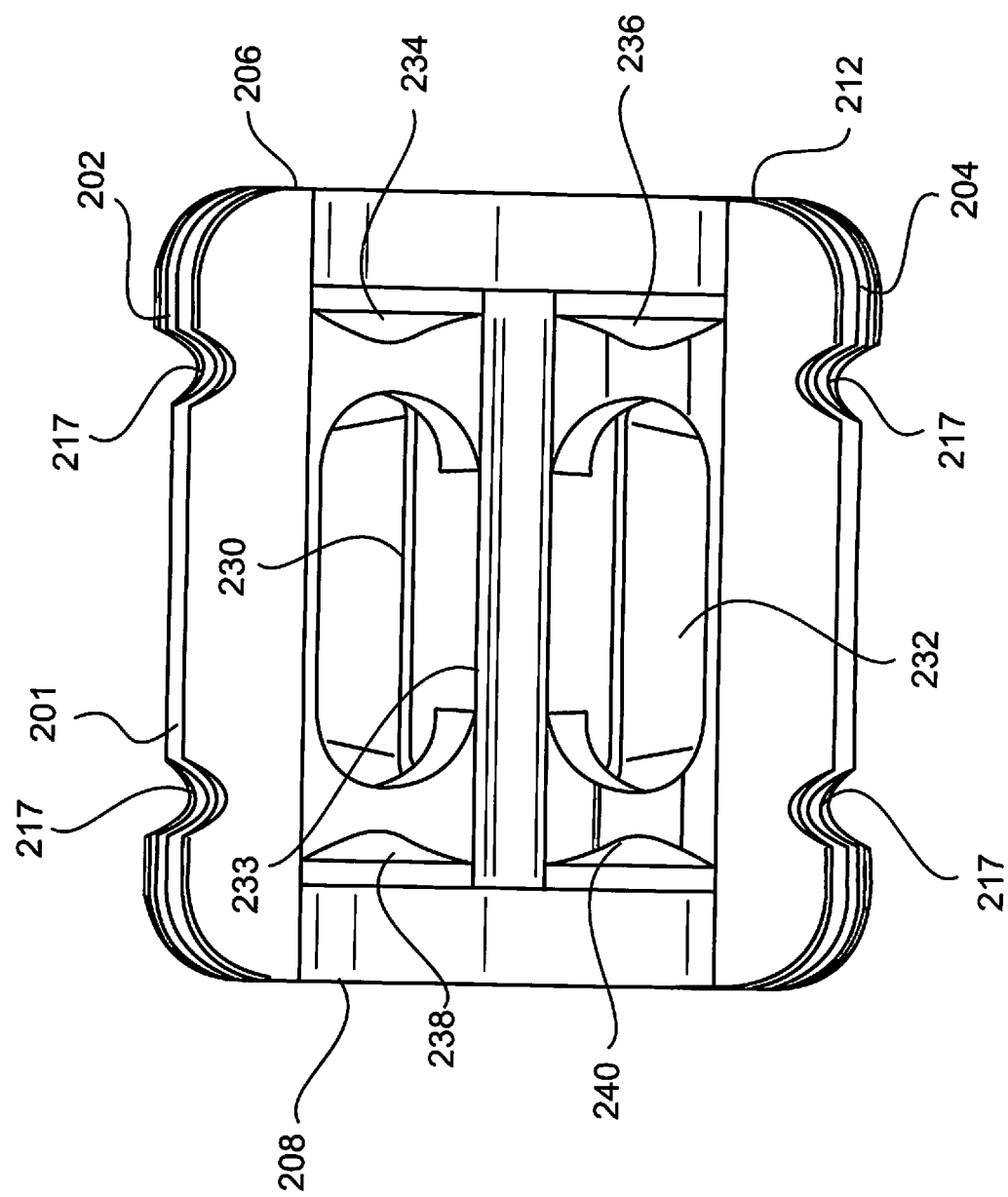
FIG. 13 depicts a rear elevational view of the spacer shown in FIG. 13.
Figure 14:
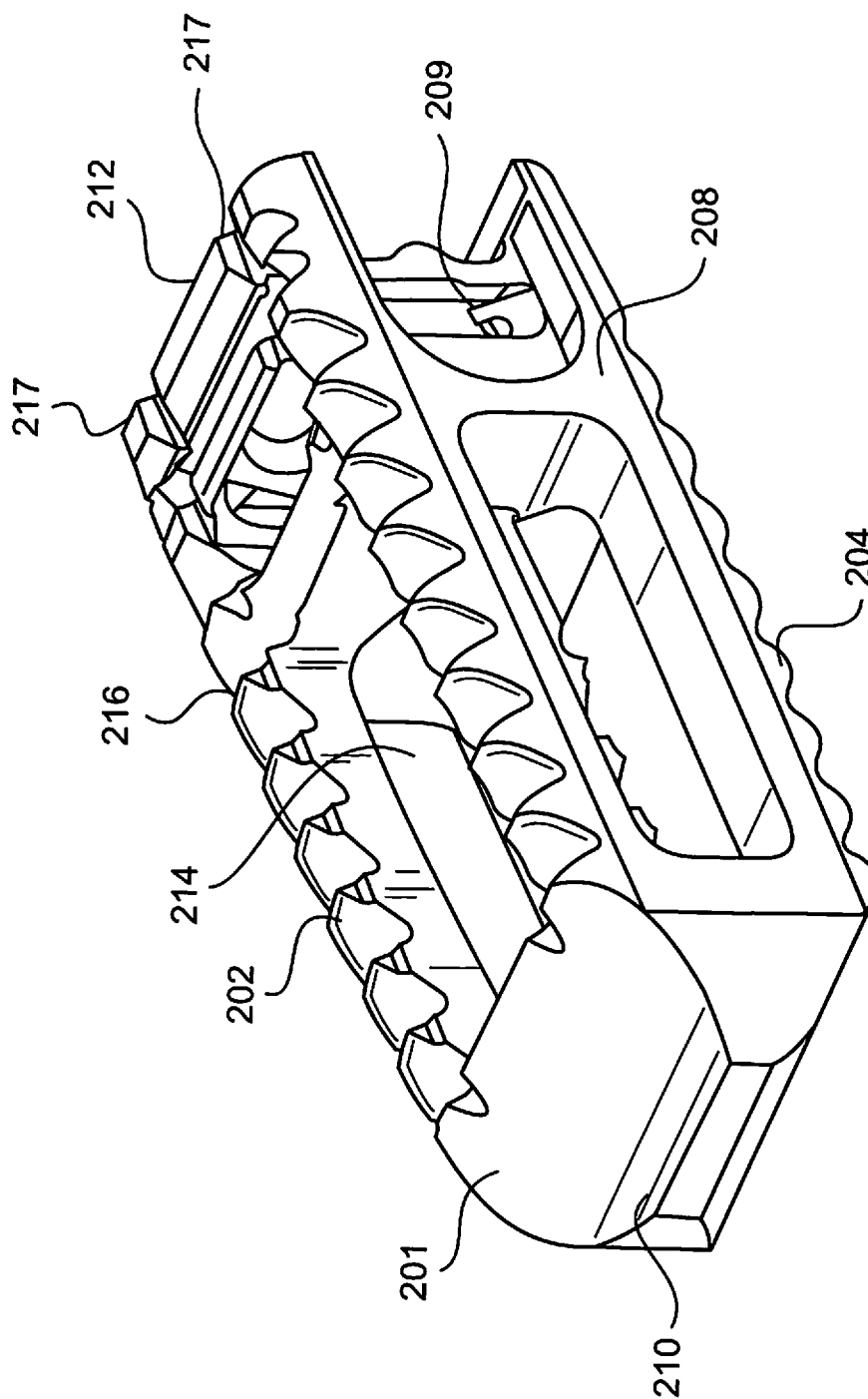
FIG. 14 depicts a perspective view of the spacer body of the spacer shown in FIG. 11, with the anchors removed.

Referring to FIG. 13, body 201 has an upper passage 230 extending between superior surface 202 and proximal end portion 212. Upper passage 230 comprises an upper track that acts as a guide to guide the deployment of upper anchor 218 into an adjacent vertebral body located superiorly of spacer 200.

Similarly, body 201 has a lower passage 232 extending between 204 inferior surface and proximal end portion 212. Lower passage 232 comprises a lower track that acts as a guide to guide the deployment of lower anchor 220 into an adjacent vertebral body located inferiorly of spacer 200. A spacer 233 extends between upper passage 230 and lower passage 232 along plane P, dividing upper passage 230 from lower passage 232.

An upper detent 234 and a lower detent 236 each extends medially from the proximal end of lateral side surface 206 into upper passage 230 and lower passage 232, respectively. Similarly, an upper detent 238 and a lower detent 240 each extends medially from the proximal end of lateral side surface 208 into upper passage 230 and lower passage 232, respectively.

Figure 15:
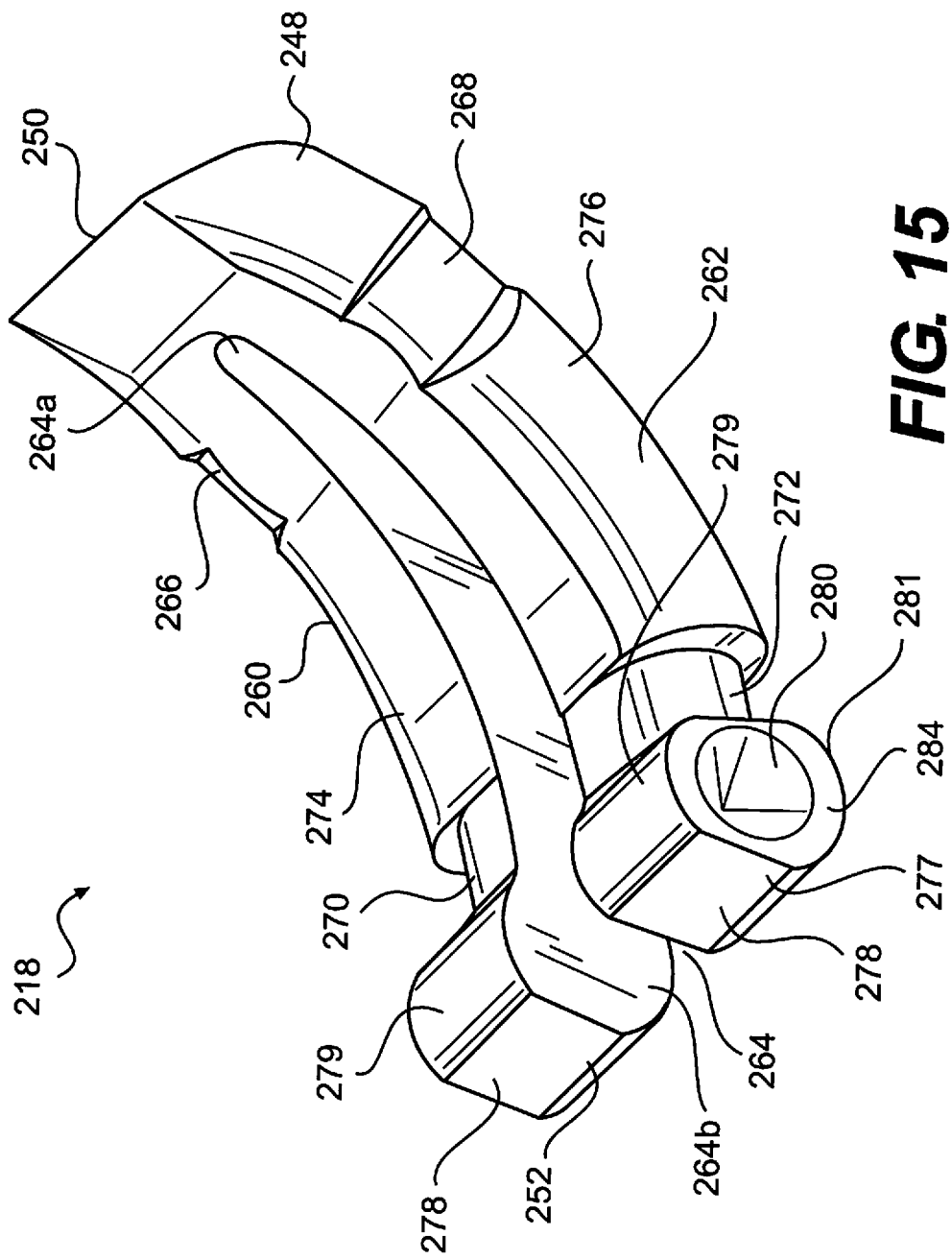
FIG. 15 depicts a perspective view of a top anchor used with the spacer shown in FIG. 14.
Figure 16:
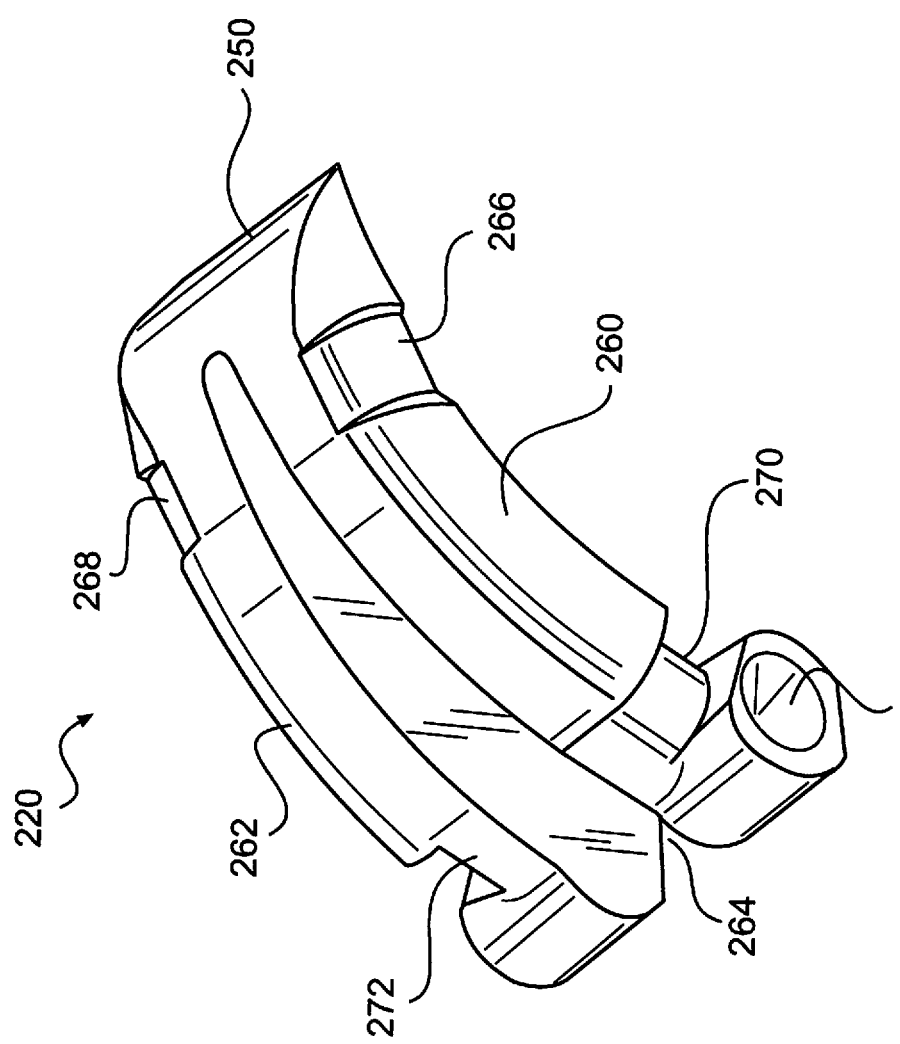
FIG. 16 depicts a perspective view of a bottom anchor used with the spacer shown in FIG. 14.

Referring to FIGS. 15 and 16, upper anchor 218 that is used to secure body 201 between superior and inferior vertebrae is shown. Lower anchor 220 is identical to upper anchor 218 and, when inserted into body 201, is a mirror image of upper anchor 218 across plane P, so only upper anchor 218 will be described.

Upper anchor 218 has a body 248 having an anchor tip 250 and a proximal end 252, located distal from anchor tip 250. Body 248 has an arcuate or curvilinear profile to enable body 248 to slide along the track of upper passage 230, as will be described in detail later herein.

Body 248 comprises a first prong 260, a second prong 262, each extending in a proximal direction away from anchor tip 250, and a central groove 264 extending between first prong 260 and second prong 262. Groove 264 tapers from a narrow end 264a proximate to anchor tip 250 to a wide end 264b proximate to proximal end 252. First prong 260, second prong 262, and central groove 264 define body 248 as a generally "V-shaped" body, with an apex of the "V"

at anchor tip 250. The central groove 264 may extend to a depth greater than and/or beyond first retention grooves 266, 268 in the anchors 218, 220.

Each of first prong 260 and second prong 262 comprises a first retention groove 266, 268 respectively, proximate to anchor tip 250 and narrow end 264a of groove 264, and a second retention groove 270, 272 distal from anchor tip 250 and proximate to wide end 264b of groove 264. For example, the retention grooves 266, 268 may be positioned at the lateral-most side surfaces of the prongs 260, 262, respectively. Body 248 extends along a first curvilinear central portion 274 extending between first retention groove 266 and second retention groove 270 and a second curvilinear central portion 276 extending between first retention groove 268 and second retention groove 272. The central portions 274, 276 extending between the first retention grooves 266, 268 and the second retention grooves 270, 272 are preferably substantially smooth and without teeth (e.g., teeth-free). Each central portion 274, 276 is tapered from a narrower end proximate to anchor tip 250 to a wider end proximate to second retention grooves 270, 272. The taper of central portions 274, 276, along with taper of central groove 264, allows for the compression of central portions 264, 276 toward each other as anchors 218, 220 are advanced.

Each of first and second prongs 260, 262 at proximal end 252 includes a proximal tip 277 adjacent to each second retention groove 270, 272. The proximal tips 277 are enlarged in dimension relative to the remainder of the anchor 218, 220. For example, the proximal tips 277 may have a height and/or width greater than the height and/or width of the remainder of the prongs 260, 262. The proximal tips 277 may be defined at least in part by the retention grooves 270, 272. Proximal tips 277 may include a generally planar proximal face 278, a curved superior surface 279 extending upwardly from proximal face 278, and a curved inferior surface 281 extending downwardly from proximal face 278.

A lateral side 284 extends laterally outwardly from each second retention groove 270, 272 and includes an insertion tool insertion indent 280, 282. Indent 280 is a generally hemispherical indent sized to accept a detent in an insertion tool (not shown). Lateral side 284 extends farther laterally outwardly than each of central portion 274, 276.

Figure 11:
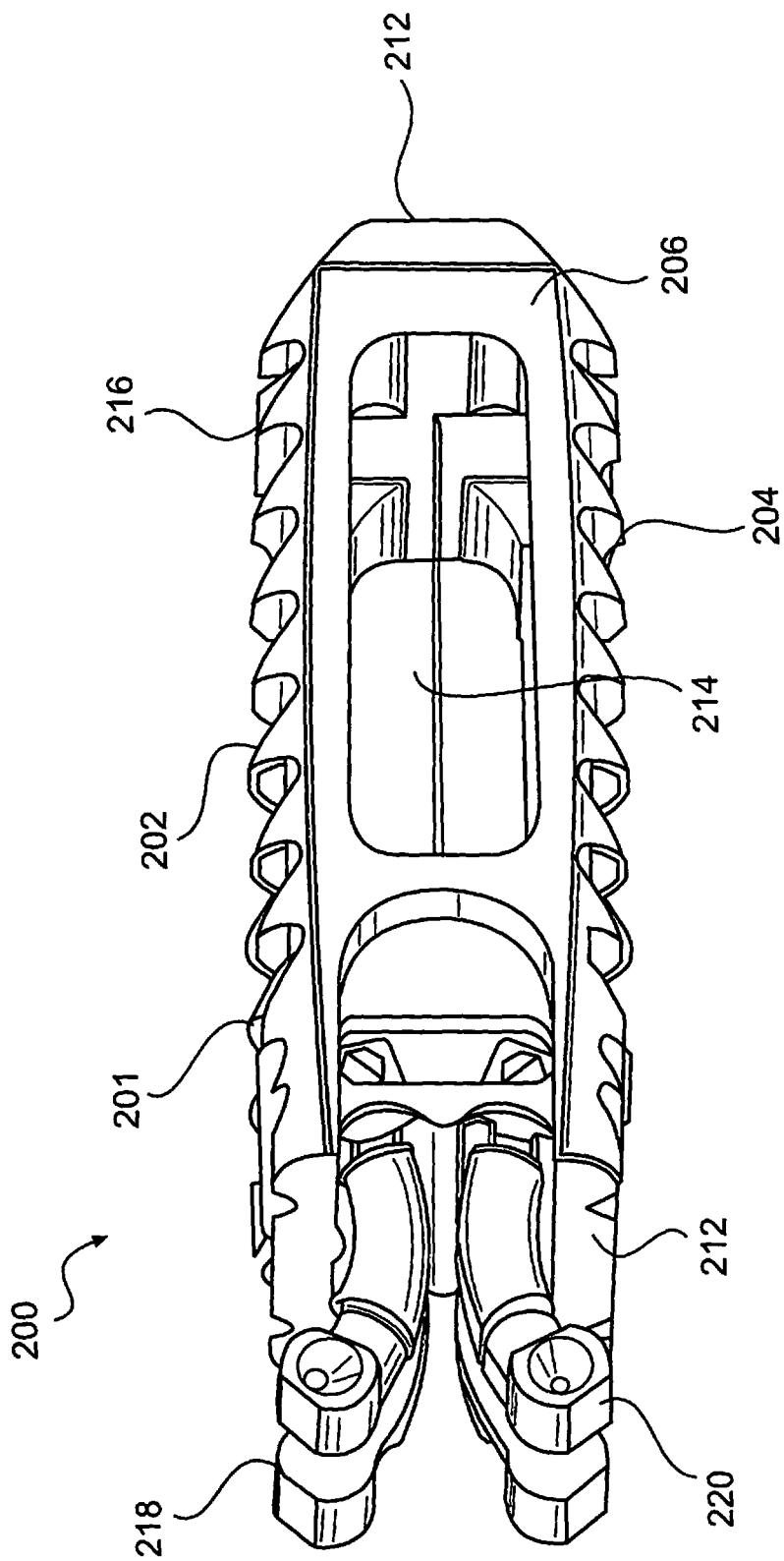
FIG. 11 depicts a rear perspective view of a spacer in accordance with an alternative embodiment of the present invention, wherein the anchor tips of upper and lower anchors of the anchoring device are disposed entirely within the spacer.
Figure 12:
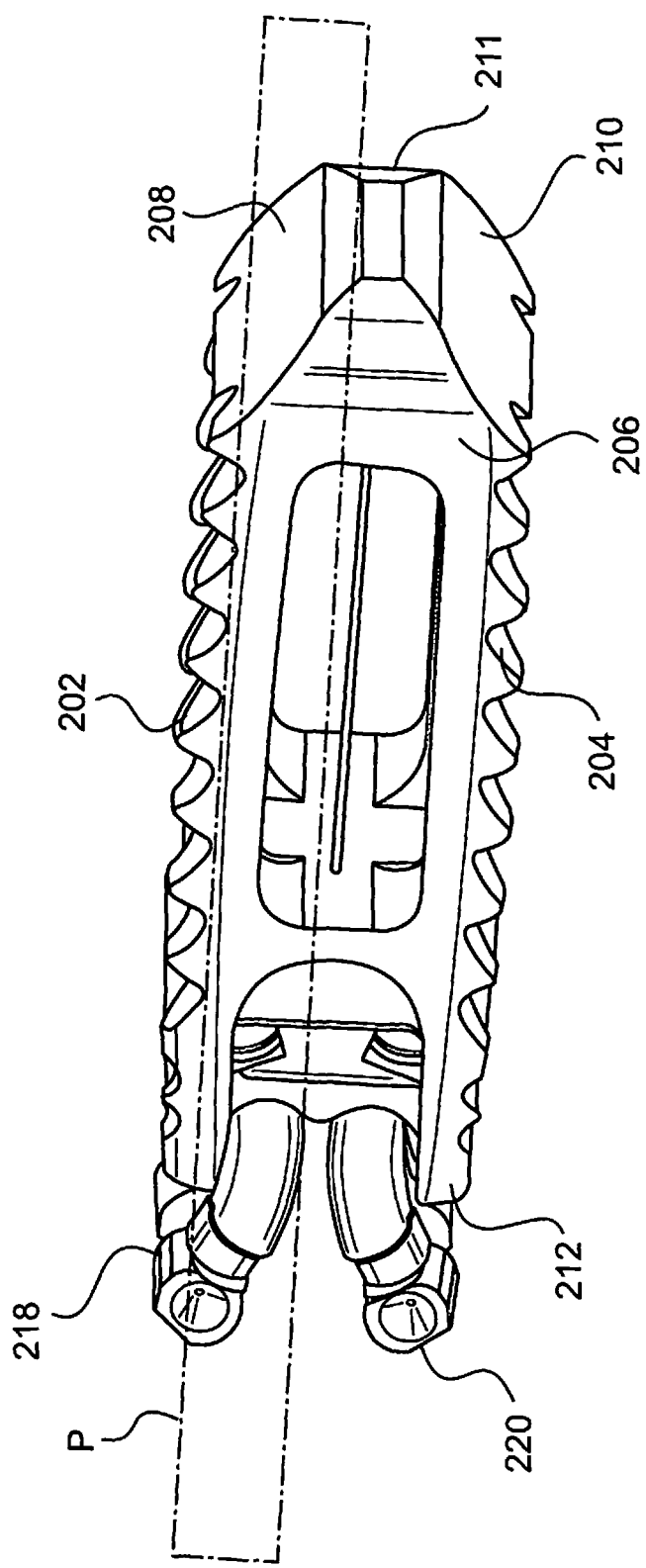
FIG. 12 depicts a perspective view of the spacer shown in FIG. 11.
Figure 17:
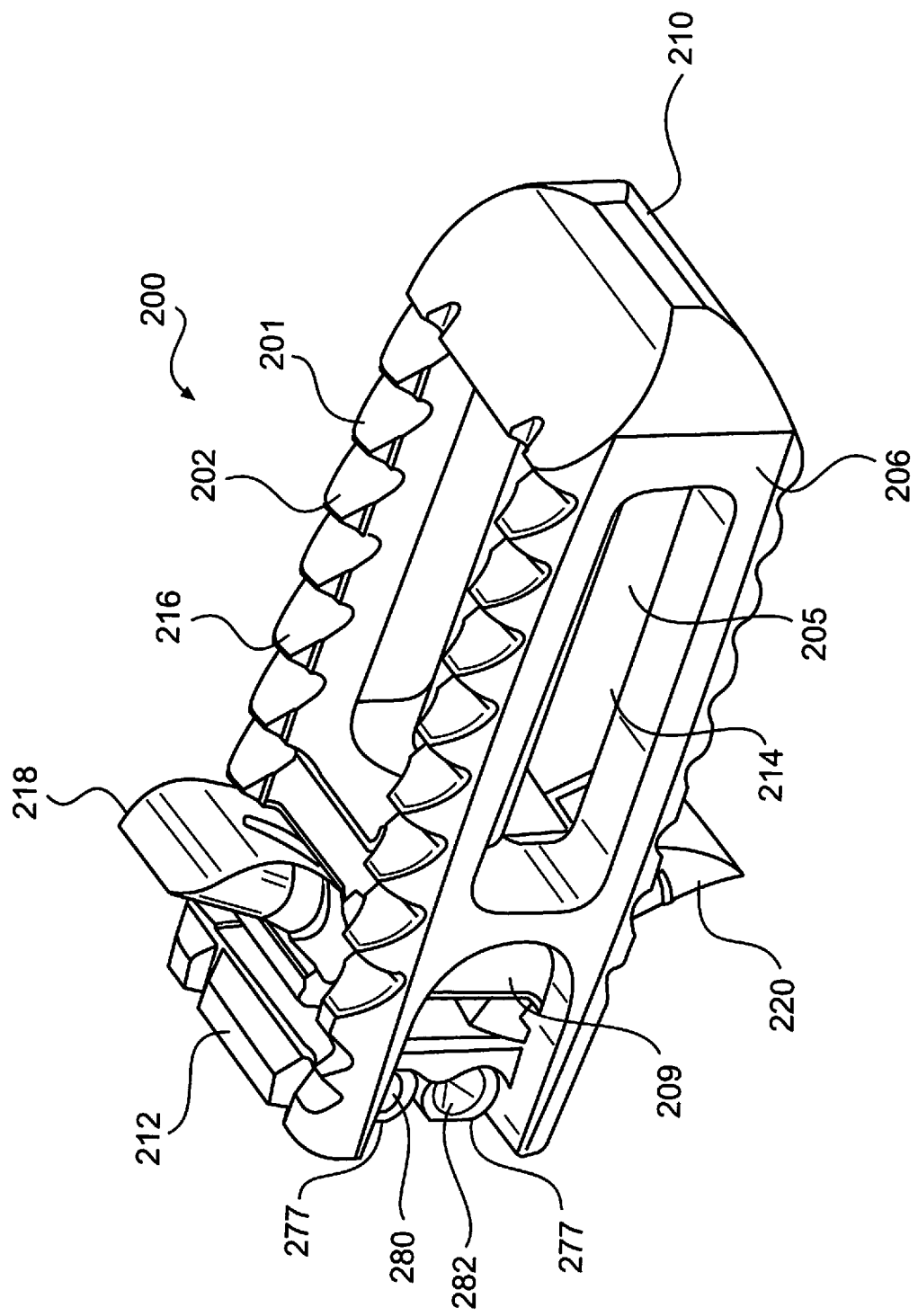
FIG. 17 depicts a perspective view of the spacer shown in FIG. 11, with the upper and lower anchors deployed.
Figure 18:
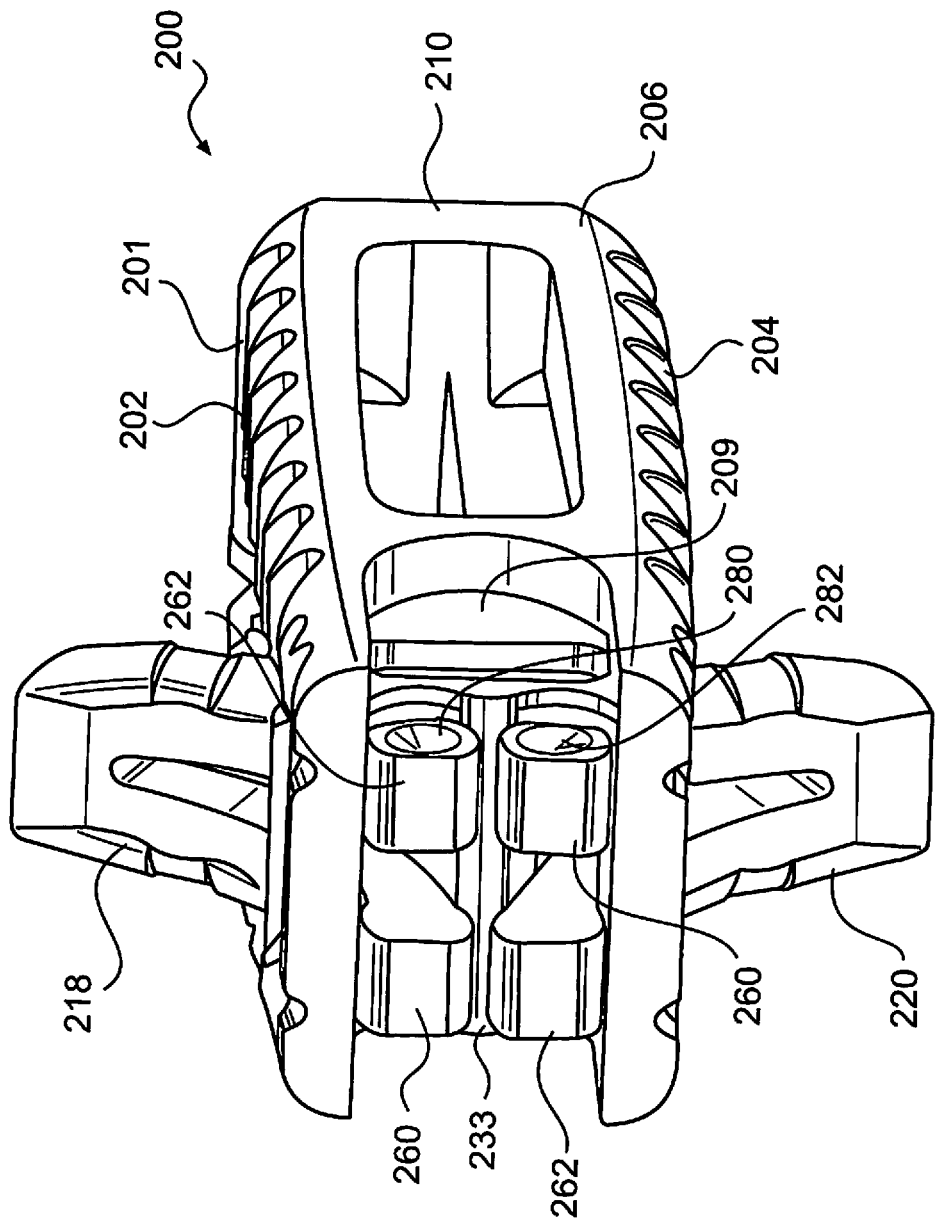
FIG. 18 depicts a rear perspective view of the spacer shown in FIG. 11, with the upper and lower anchors deployed.

As shown in FIGS. 11 and 12, anchors 218, 220 are slidingly disposed in a first position in upper passage 230 along its upper track and lower passage 232 along its lower track, respectively, wherein each anchor 218, 220 has anchor tip 250 located within body 201. Preferably, the upper passage 230 and lower passage 232 are centered between the lateral sides surfaces 206, 208 such that the anchors 218, 220 are also centrally positioned between the lateral side surfaces 206, 208. FIGS. 17 and 18 show anchors 218, 220 in a second position wherein each anchor 218, 220 have anchor tip 250 extending outwardly from superior surface 202 and inferior surface 204, respectively, after anchors 218, 220 have been radially deployed out of body 201 from the first position to the second position.

Each of upper anchor 218 and lower anchor 220 are separate elements that slide independently of each other along their respective upper and lower tracks when a force is applied to each of upper and lower anchors 218, 220, respectively.

When anchors 218, 220 are in the position shown in FIGS. 11 and 12, detents 234, 238 are removably inserted into and engaged with first retention grooves 268, 266, respectively. An insertion tool (not shown) is used to insert spacer 200 between two adjacent vertebrae (not shown). The insertion can be performed from either an anterior-to-posterior direction or a lateral direction. Once body 201 is between the vertebrae, another insertion tool or the same insertion tool (not shown) having detents corresponding to insertion indents 280, 282 is attached to anchors 218, 220 at insertion indents 280, 282. The insertion tool compresses first prong 260 and second prong 262 toward each other, shrinking the width of central groove 264 and pulling retention grooves 266, 268 away from respective detents 234, 236, 238, 240 so that the insertion tool can advance anchors 218, 220 to the point that proximal tips 250 extend outwardly from body 201 as anchors 218, 220 slide along the tracks in upper passage 230 and lower passage 232, respectively, to the position shown in FIGS. 17 and 18, in which proximal ends 277 are located within body 201 such that proximal end portion 277 is co-planar with proximal end portion 212 or within body 201 inside the plane defined by proximal end portion 212. Also, inferior surface 281 engages spacer 233 (shown in FIG. 18), restricting further advancement of anchors 218, 220.

At this point, the insertion tool is removed, and first prong 260 and second prong 262 bias away from each other, enlarging the width of central groove 264, so that detents 234, 236, 238, 240 engage with second grooves 270, 272, securing anchors 218, 220 and preventing anchors 218, 220 from moving out of their respective vertebrae. Further, lateral side 284 is retained inside body 201 so as not to extend laterally beyond either of lateral side surfaces 206, 208. Additionally, the lateral extension of distal tip 278 beyond that of each central portion 274, 276 extends laterally of detents 234, 236, 238, 240, further locking detents 234, 236, 238, 240 into their respective second grooves 270, 272.

It is to be understood that the disclosure describes a few embodiments and that many variations of the invention can easily be devised by those skilled in the art after reading this disclosure and that the scope of the present invention is to be determined by the following claims.

What is claimed is:

1. An intervertebral fusion device comprising:
    a spacer having superior and inferior surfaces adapted to be implanted between an upper vertebral body and a lower vertebral body and lateral sides surfaces connecting the superior and inferior surfaces; and
    an anchoring device defining a central longitudinal axis and having a body with an anchor tip and a proximal end, located proximal from anchor tip, and a central groove, wherein the proximal end is separated by the central groove, the anchoring device being movable between a first position wherein the anchor tip is disposed inside the spacer and a second position wherein the anchor tip is extended outwardly from the spacer, wherein the central longitudinal axis of the anchoring device is centrally positioned between the lateral side surfaces of the spacer
    wherein the anchoring device includes a first prong and a second prong, and
    wherein each of the first and second prongs has a curvilinear central portion extending between a first retention groove and a second retention groove.

2. The intervertebral fusion device claim 1, wherein the anchoring device comprises an upper anchor and a lower anchor.

3. The intervertebral fusion device claim 2, wherein the spacer comprises an upper guide and a lower guide such that each of the upper guide and the lower guide is adapted to respectively guide the deployment of the upper anchor and the lower anchor into their respective vertebral bodies.

4. The intervertebral fusion device claim 3, wherein the upper and lower anchors are separate elements that slide independently of each other along their respective upper and lower guides when a force is applied to each of the upper and lower anchors.

5. The intervertebral fusion device claim 2, wherein each of the upper anchor and the lower anchor comprises:
the first prong extending in a proximal direction away from the anchor tip;
the second prong extending in a proximal direction away from the anchor tip; and
the central groove extending between the first prong and the second prong.

6. The intervertebral fusion device claim 5, wherein the central groove tapers from a narrow end proximate to the anchor tip to a wide end proximate to the proximal end.

7. The intervertebral fusion device claim 6, wherein each of the first and second prongs comprises the first retention groove proximate to the narrow end and the second retention groove proximate to the wide end.

8. The intervertebral fusion device claim 7, wherein each of the first and second prongs comprises removal tool insertion indent extending along a lateral side of each of the first and second prongs.

9. An intervertebral fusion device comprising:
an implant body having a superior surface and an opposing inferior surface and lateral sides connecting the superior and inferior surfaces and a proximal end and a distal end, each extending between the superior surface and the inferior surface, wherein the body further includes an upper track extending from the proximal end to the superior surface and a lower track extending from the proximal end to the inferior surface;
an upper anchor defining a central longitudinal axis and having an upper anchor tip slidingly disposed along the upper track such that upper anchor tip is movable from a first position inside the body to a second position, extending outwardly from the superior surface; and
a lower anchor defining a central longitudinal axis and having a lower anchor tip slidingly disposed along the lower track such that lower anchor tip is movable from a first position inside the body to a second position, extending outwardly from the inferior surface, wherein at least one of the central longitudinal axis of the upper anchor and the central longitudinal axis of the lower anchor is centrally positioned between the lateral side surfaces of the implant body,
wherein the arcuate body comprises a first prong, a second prong, and a central groove extending between the first prong and the second prong, wherein each of the first prong and the second prong comprises a first groove proximate to the anchor tip and a second groove distal from the anchor tip, and
wherein the implant body comprises a pair of generally parallel lateral sides extending between the proximal end and the distal end, and an upper detent and a lower detent extending medially from the proximal end of each of the lateral sides such that the upper detent is removably inserted into the first groove of the upper anchor when the upper anchor is in the first position and wherein the upper detent is removably inserted into the second groove of the upper anchor when the upper anchor is in the second position.

10. The intervertebral fusion device claim 9, wherein each of the upper anchor and the lower anchor comprises an arcuate body extending between the anchor tip and a proximal end.

11. The intervertebral fusion device claim 9, wherein the body further comprises a spacer separating the upper detent from the lower detent.

12. The intervertebral fusion device claim 9, wherein the upper and lower anchors are housed within the implant body, and wherein the upper and lower anchors radially deploy out of the implant body from the first position to the second position.

13. An intervertebral fusion device comprising:
an implant body having a superior surface, an opposing inferior surface, lateral sides connecting the superior and inferior surfaces, and a proximal end extending between the superior surface and the inferior surface, an upper passage extending between the superior surface and the proximal end; and a lower passage extending between the inferior surface and the proximal end;
an upper anchor sliding disposed in the upper passage between a first upper anchor position and a second upper anchor position, the upper anchor defining a central longitudinal axis and having an upper anchor tip disposed within the body when the upper anchor is in the first upper anchor position and wherein the upper anchor tip extends outwardly from the superior surface when the upper anchor is in the second upper anchor position; and
a lower anchor slidingly disposed in the lower passage between a first lower anchor position and a second lower anchor position, the lower anchor defining a central longitudinal axis and having a lower anchor tip disposed within the body when the lower anchor is in the first lower anchor position and wherein the lower anchor tip extends outwardly from the inferior surface when the lower anchor is in the second lower anchor position, wherein the at least one of the central longitudinal axis of the upper anchor and the central longitudinal axis of the lower anchor is centrally positioned between the lateral sides surfaces of the implant body,
wherein each of the upper anchor comprises a first groove proximate to the anchor tip and a second groove distal from the anchor tip, and wherein the body comprises a detent engaged with the first groove when the upper anchor is in the first upper anchor position and wherein the detent is engaged with the second groove when the upper anchor is in the second upper anchor position.

14. The intervertebral fusion device claim 13, wherein each of the upper anchor and the lower anchor comprises an arcuate body extending away from the anchor tip.

15. The intervertebral fusion device claim 14, wherein the arcuate body comprises a first prong and a second prong each extending proximally from the anchor tip and a central groove extending between the first prong and the second prong, wherein the central groove tapers from narrower to wider from the anchor tip.

* * * * *